United States Patent [19]

Robl

[11] Patent Number: 5,750,687
[45] Date of Patent: May 12, 1998

US005750687A

[54] AZEPINONE COMPOUNDS USEFUL IN THE INHIBITION OF ACE AND NEP

[75] Inventor: Jeffrey A. Robl, Newtown, Pa.

[73] Assignee: Bristol-Myers Squibb Company, Princeton, N.J.

[21] Appl. No.: 700,251

[22] Filed: Aug. 20, 1996

Related U.S. Application Data

[62] Division of Ser. No. 390,717, Feb. 17, 1995, Pat. No. 5,587,375.

[51] Int. Cl.$^6$ .................. C07C 223/12; C07C 405/06; A61K 31/55
[52] U.S. Cl. .................. 540/527; 514/212; 514/79; 540/524; 540/528; 540/487
[58] Field of Search .................. 540/527, 524, 540/528, 487; 514/212, 79

[56] References Cited

U.S. PATENT DOCUMENTS

| | | | |
|---|---|---|---|
| 3,856,798 | 12/1974 | Meyer et al. | 260/294.8 |
| 4,105,776 | 8/1978 | Ondetti et al. | 424/274 |
| 4,186,200 | 1/1980 | Kubo et al. | 424/256 |
| 4,192,945 | 3/1980 | Ondetti | 546/245 |
| 4,225,495 | 9/1980 | Ondetti | 260/244.4 |
| 4,337,201 | 6/1982 | Petrillo, Jr. | 548/413 |
| 4,339,600 | 7/1982 | Ondetti et al. | 562/426 |
| 4,374,829 | 2/1983 | Harris et al. | 424/177 |
| 4,409,146 | 10/1983 | Thorsett et al. | 260/239.3 |
| 4,410,520 | 10/1983 | Watthey | 424/244 |
| 4,415,496 | 11/1983 | Harris et al. | 260/239.3 |
| 4,432,971 | 2/1984 | Karanewsky et al. | 424/177 |
| 4,432,972 | 2/1984 | Karanewsky et al. | 424/177 |
| 4,460,579 | 7/1984 | Karanewsky | 424/200 |
| 4,465,679 | 8/1984 | Huang et al. | 424/244 |
| 4,470,988 | 9/1984 | Watthey | 424/263 |
| 4,473,575 | 9/1984 | Watthey | 424/263 |
| 4,477,464 | 10/1984 | Slade et al. | 424/275 |
| 4,512,924 | 4/1985 | Attwood et al. | 260/243.3 |
| 4,537,885 | 8/1985 | Watthey | 514/183 |
| 4,539,150 | 9/1985 | Katakami et al. | 260/239.3 |
| 4,548,932 | 10/1985 | Sugihara et al. | 514/211 |
| 4,575,503 | 3/1986 | Watthey | 514/213 |

(List continued on next page.)

FOREIGN PATENT DOCUMENTS

| | | |
|---|---|---|
| 049505 | 4/1982 | European Pat. Off. |
| 128728 | 12/1984 | European Pat. Off. |
| 220865 | 5/1987 | European Pat. Off. |
| 249223 | 12/1987 | European Pat. Off. |
| 249224 | 12/1987 | European Pat. Off. |
| 481522 | 4/1992 | European Pat. Off. |
| 524553 | 1/1993 | European Pat. Off. |
| 534363 | 3/1993 | European Pat. Off. |
| 534396 | 3/1993 | European Pat. Off. |
| 534492 | 3/1993 | European Pat. Off. |
| 595610 | 5/1994 | European Pat. Off. |
| 599444 | 6/1994 | European Pat. Off. |
| 629627 | 12/1994 | European Pat. Off. |
| 2543553 | 10/1984 | France |
| 2207351 | 2/1989 | United Kingdom |
| WO93/16103 | 8/1993 | WIPO |
| WO94/10193 | 5/1994 | WIPO |
| WO94/26719 | 11/1994 | WIPO |
| WO94/28901 | 12/1994 | WIPO |

OTHER PUBLICATIONS

Sreenivasan, U. et al *J. Med. Chem.* 36, 256–263 (1993).
Adams et al., Synthetic Communications, vol. 18, 2225–2231 (1988).
Attwood et al., FEBS Letters, vol. 165, pp. 201–206 (1984).
Attwood et al., J. Chem. Soc. Perkin Trans I (1986) pp. 1011–1019.

(List continued on next page.)

*Primary Examiner*—Mukund J. Shah
*Assistant Examiner*—King Lit Wong
*Attorney, Agent, or Firm*—Suzanne E. Babajko

[57] ABSTRACT

Compounds having the following formulae I and II, and pharmaceutically acceptable salts thereof, including dual inhibitors of ACE and NEP and selective ACE inhibitors:

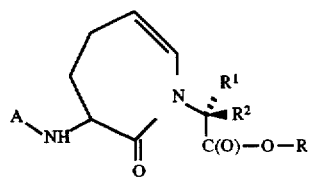

(I)

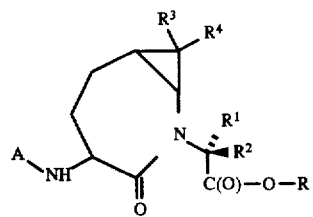

(II)

wherein:
A is

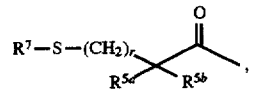

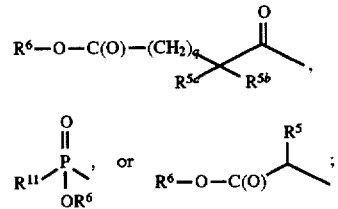

and wherein R, $R^1$, $R^2$, $R^3$, $R^4$, $R^5$, $R^{5a}$, $R^{5b}$, $R^6$, $R^7$, $R^{11}$, q and r are defined herein.

14 Claims, No Drawings

U.S. PATENT DOCUMENTS

| | | | |
|---|---|---|---|
| 4,584,294 | 4/1986 | Ruyle | 514/214 |
| 4,587,050 | 5/1986 | Harris et al. | 260/239.3 |
| 4,587,238 | 5/1986 | Harris et al. | 514/183 |
| 4,594,341 | 6/1986 | Cheung et al. | 514/211 |
| 4,617,301 | 10/1986 | Patchett et al. | 514/214 |
| 4,629,787 | 12/1986 | Harris et al. | 540/528 |
| 4,680,392 | 7/1987 | Harris et al. | 540/527 |
| 4,699,905 | 10/1987 | Yanagisawa et al. | 514/211 |
| 4,711,884 | 12/1987 | Karanewsky | 514/226 |
| 4,722,810 | 2/1988 | Delaney et al. | 260/402.5 |
| 4,734,410 | 3/1988 | Yanagisawa et al. | 514/212 |
| 4,749,688 | 6/1988 | Haslanger et al. | 514/19 |
| 4,801,609 | 1/1989 | Haslanger et al. | 514/506 |
| 4,824,832 | 4/1989 | Flynn et al. | 514/214 |
| 4,857,520 | 8/1989 | Urbach et al. | 514/183 |
| 4,873,235 | 10/1989 | Parsons et al. | 514/312 |
| 4,879,309 | 11/1989 | Doll et al. | 514/513 |
| 4,963,539 | 10/1990 | Delaney | 514/119 |
| 4,973,585 | 11/1990 | Flynn et al. | 514/214 |
| 5,061,710 | 10/1991 | Haslanger et al. | 514/266 |
| 5,075,302 | 12/1991 | Neustadt | 514/211 |
| 5,098,934 | 3/1992 | Vevert et al. | 514/513 |
| 5,190,974 | 3/1993 | Clemence et al. | 514/513 |
| 5,208,236 | 5/1993 | Neustadt | 514/237.5 |
| 5,223,516 | 6/1993 | Delaney et al. | 514/339 |
| 5,225,401 | 7/1993 | Seymour | 519/19 |
| 5,232,920 | 8/1993 | Neustadt | 514/212 |
| 5,238,924 | 8/1993 | Smith | 514/19 |
| 5,262,436 | 11/1993 | Haslanger et al. | 514/513 |
| 5,362,727 | 11/1994 | Robl | 514/214 |
| 5,366,973 | 11/1994 | Flynn et al. | 514/221 |
| 5,508,272 | 4/1996 | Robl | 514/80 |

OTHER PUBLICATIONS

Bolos et al., J. Org. Chem., 57, 3535–3539 (1992).

Bolos et al., Tetrahedron, vol. 48, pp. 9567–9576 (1992).

Boyer, T. D. "Cirrhosis of the Liver and Its Major Sequelae" in: Wyngaarden, J. B. et al., Cecil Textbook of Medicine, vol. 1 (Saunders Co., 1992) pp. 786–789.

Chackalamannil et al., Bioorganic & Medicinal Chemistry Letters, vol. 2, pp. 1003–1006 (1992).

Das et al., Bioorganic & Medicinal Chemistry Letters, vol. 4, pp. 2193–2198 (1994).

Delaney et al., Bioorganic & Medicinal Chemistry Letters, vol. 4, pp. 1783–1788 (1994).

Dussaule et al., Jour. of Clinical Endocrinology and Metabolism, vol. 72, pp. 653–659 (1991).

Fernandez-Cruz, The Lancet, Dec. 21/28, pp. 1439–1440 (1985).

Flynn et al., J. Med. Chem., 36, pp. 2420–2423 (1993).

Flynn, Tetrahedron Letters, vol. 31, pp. 815–818 (1990).

Fobian et al., 206th Meeting of the Amer. Chem. Society, Aug. 1993 Abstr. ORG 297.

Fyhrquist et al., The Lancet, Dec. 21/28, p. 1439 (1985).

Hanau et al., 206th Meeting of the Amer. Chem. Society, Aug. 1993 Abstr. ORG 298.

Itoh et al., Chem. Pharm. Bull., vol. 34, pp. 1128–1147, 2078–2089 (1986).

Laffi et al., Gastroenterology, vol. 96, pp. 167–177 (1989).

Moeller et al., Tetrahedron Letters, vol. 33, pp. 6041–6044 (1992).

Naming and Indexing of Chemical Substances for Chemical Abstracts, 1987 Index Guide, Section 203.

Natoff et al., Drugs Of the Future, vol. 12, pp. 475–483 (1987).

Parsons et al., Biochem and Biophysical Research Comm. 117, pp. 108–113 (1983).

Robl et al., Bioorganic & Medicinal Chem. Letters, vol. 4, pp. 1795–1800 (1994).

Robl et al., Bioorganic & Medicinal Chemistry Letters, vol. 4, pp. 1789–1794, 2055–2060 (1994).

Robl et al., J. Am. Chem. Soc., 116, pp. 2348–2355 (1994).

Robl, Tetrahedron Letters, vol. 35, pp. 393–396, 1393–1396 (1994).

Slade et al., J. Med. Chem., 28, pp. 1517–1521 (1985).

Smith et al., Biochemistry, vol. 14, pp. 766–771 (1975).

Thorsett et al., J. Med. Chem., 29, pp. 251–260 (1986).

Thorsett, Actual Chim. Ther., vol. 13, pp. 257–268 (1986).

Watthey et al., J. Med. Chem., 28, pp. 1511–1516 (1985).

Yanagisawa et al., J. Med. Chem., 30, pp. 1984–1991 (1987).

Yanagisawa et al., J. Med. Chem., 31, pp. 422–428 (1988).

AZEPINONE COMPOUNDS USEFUL IN THE INHIBITION OF ACE AND NEP

This is a division of application Ser. No. 08/390,717, filed Feb. 17, 1995, now U.S. Pat. No. 5,587,375.

FIELD OF THE INVENTION

The present invention is directed to novel unsaturated and cyclopropyl-substituted azepinone compounds which are useful either as selective angiotensin converting enzyme inhibitors, or as dual inhibitors of both angiotensin converting enzyme and neutral endopeptidase. The present invention is also directed to pharmaceutical compositions containing such selective or dual action inhibitors and to methods of using such compositions, as well as to processes for preparing the novel inhibitors, novel intermediates, and processes for preparing such intermediates.

SUMMARY OF THE INVENTION

The novel azepinones of this invention include those compounds having the following formulae I and II, and pharmaceutically acceptable salts thereof:

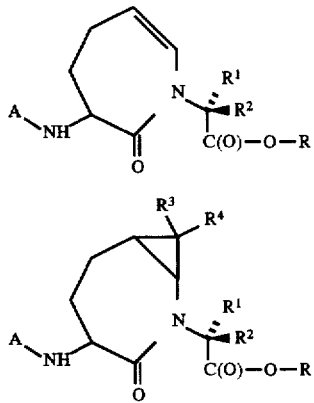

wherein:

A is

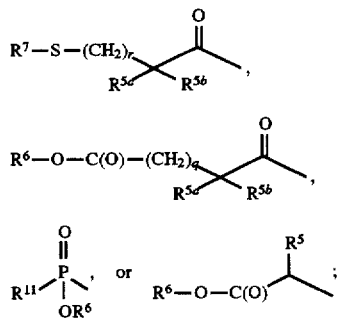

R and $R^6$ are each independently hydrogen, alkyl, substituted alkyl, aryl—$(CH_2)_p$—, substituted aryl—$(CH_2)_p$—, heteroaryl—$(CH_2)_p$—, —$CH(R^8)$ —O—C(O)—$R^9$, or

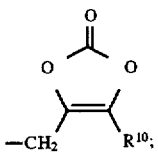

$R^1$ and $R^2$ are each independently hydrogen, alkyl, substituted alkyl, cycloalkyl—$(CH_2)_p$—, aryl—$(CH_2)_p$—, substituted aryl—$(CH_2)_p$—, heteroaryl—$(CH_2)_p$—, or $R^1$ and $R^2$ may form, together with the carbon to which they are bonded, a 3 to 7 membered carbocyclic ring, where said ring is optionally substituted by alkyl, or by aryl which is fused or bonded by a single bond to said ring;

$R^3$ and $R^4$ are each independently hydrogen, alkyl, aryl, halo, or —C(O)—OR, where R is as defined above;

$R^5$, $R^{5a}$, and $R^{5b}$ are each independently hydrogen, alkyl, alkenyl, cycloalkyl, substituted alkyl, substituted alkenyl, aryl, substituted aryl, heteroaryl, cycloalkyl-alkylene-, aryl-alkylene-, substituted aryl-alkylene-, and heteroaryl-alkylene-, or $R^{5a}$ and $R^{5b}$ may form, together with the carbon to which they are bonded, a 3 to 7 membered carbocyclic ring, where said ring is optionally substituted by alkyl, or by aryl which is fused or bonded by a single bond to said ring;

$R^7$ is hydrogen, $R^8$—C(O)—, or $R^{12}$—S—; $R^8$ is hydrogen, alkyl, substituted alkyl, cycloalkyl—$(CH_2)_p$—, aryl—$(CH_2)_p$—, substituted aryl—$(CH_2)_p$—, or heteroaryl—$(CH_2)_p$—;

$R^9$ is hydrogen, alkyl, alkoxy, or aryl;

$R^{10}$ is alkyl or aryl—$(CH_2)_p$—;

$R^{11}$ is alkyl, substituted alkyl, cycloalkyl—$(CH_2)_p$—, aryl—$(CH_2)_p$—, substituted aryl—$(CH_2)_p$—, or heteroaryl—$(CH_2)_p$—;

$R^{12}$ is hydrogen, alkyl, substituted alkyl, cycloalkyl—$(CH_2)_p$—, aryl—$(CH_2)_p$—, substituted aryl—$(CH_2)_p$—, or heteroaryl—$(CH_2)_p$—, or —S—$R^{12}$ completes a symmetrical disulfide wherein $R^{12}$ is

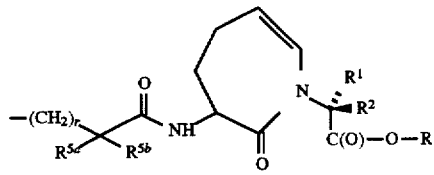

when said compound is a compound of the formula I, or

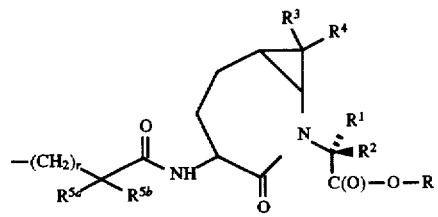

when said compound is a compound of the formula II;
p is zero or an integer from 1 to 6;
q is zero or an integer from 1 to 3; and
r is zero or one.

DETAILED DESCRIPTION OF THE INVENTION

The invention is described in further detail as follows.

Definitions

The term "alkyl", refers to straight or branched chain radicals having one to seven carbon atoms, such as methyl, ethyl, n-propyl, isopropyl, tert-butyl, or n-butyl. The term "lower alkyl" refers to straight or branched chain radicals having one to four carbon atoms, and is a preferred sub-grouping for the term alkyl.

The term "substituted alkyl" refers to such straight or branched chain radicals of 1 to 7 carbons wherein one or more, preferably one, two, or three, hydrogens have been replaced by a hydroxy, amino, cyano, halo, trifluoromethyl, —NH(lower alkyl), —N(lower alkyl)$_2$, lower alkoxy, lower alkylthio, or carboxy group.

The term "alkylene" refers to divalent straight or branched chain radicals having one to seven carbon atoms, such as —CH$_2$—, —(CH$_2$)$_2$—, —(CH$_2$)$_3$—, —(CH$_2$)$_4$—,

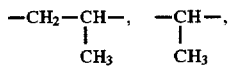

etc.

The terms "lower alkoxy" and "lower alkylthio" refer to such lower alkyl groups as defined above attached to an oxygen or sulfur, respectively.

The term "alkenyl" refers to straight or branched chain radicals of 2 to 7 carbon atoms having one or two double bonds. Preferred "alkenyl" groups are straight chain radicals of 3 to 5 carbons having one double bond.

The term "substituted alkenyl" refers to such straight or branched radicals of 2 to 7 carbons having one or two double bonds wherein a hydrogen has been replaced by a hydroxy, amino, halo, trifluoromethyl, cyano, —NH(lower alkyl), —N(lower alkyl)$_2$, lower alkoxy, lower alkylthio, or carboxy group.

The term "cycloalkyl" refers to saturated rings of 3 to 7 carbon atoms with cyclopropyl, cyclobutyl, cyclopentyl, and cyclohexyl being most preferred.

The term "carbocyclic ring" refers to a ring moiety wherein all of the ring atoms are carbon atoms.

The term "aryl" refers to phenyl, 1-naphthyl, and 2-naphthyl. The term "substituted aryl" refers to phenyl, 1-naphthyl, and 2-naphthyl having a substituent selected from lower alkyl, lower alkoxy, lower alkylthio, halo, hydroxy, trifluoromethyl, amino, —NH(lower alkyl), or —N(lower alkyl)$_2$, and di- and tri-substituted phenyl, 1-naphthyl, or 2-naphthyl wherein said substituents are selected from methyl, methoxy, methylthio, halo, hydroxy, and amino.

The term "heteroaryl" refers to unsaturated rings of 5 or 6 atoms containing one or two O and/or S atoms and/or one to four N atoms provided that the total number of hetero atoms in the ring is 4 or less. The heteroaryl ring is attached by way of an available carbon or nitrogen atom. Preferred heteroaryl groups include 2-, 3-, or 4-pyridyl, 4-imidazolyl, 4-thiazolyl, 2- and 3-thienyl, and 2- and 3-furyl. The term heteroaryl also includes bicyclic rings wherein the five or six membered ring containing O, S, and/or N atoms as defined above is fused to a benzene or pyridyl ring. Preferred bicyclic rings are 2- and 3-indolyl and 4- and 5-quinolinyl. The mono or bicyclic heteroaryl ring can also be additionally substituted at an available carbon atom by a lower alkyl, halo, hydroxy, benzyl, or cyclohexylmethyl group. Also, if the mono or bicyclic ring has an available N-atom, such N atom can also be substituted by an N-protecting group such as

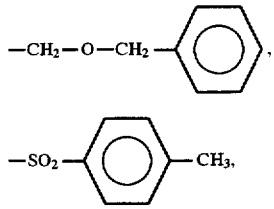

2,4-dinitrophenyl, lower alkyl, benzyl, or benzhydryl.

The terms "halogen" or "halo" refer to chlorine, bromine, fluorine and iodine.

The term "salt(s)" denotes acidic and/or basic salts formed with inorganic and/or organic acids and bases. Zwitterions (internal or inner salts) are included within the term "salt(s)" as used herein, as are quaternary ammonium salts such as alkylammonium salts. The nontoxic, pharmaceutically acceptable salts are preferred, although other salts may be useful, for example, in isolation or purification steps which may be employed during preparation.

Exemplary acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pectinate, persulfate, 3-phenylpropionate, picrate, pivalate, propionate, succinate, tartrate, thiocyanate, tosylate, and undecanoate.

Exemplary basic salts include ammonium salts, alkali metal salts such as sodium, lithium, and potassium salts, alkaline earth metal salts such as calcium and magnesium salts, salts with organic bases such as amines (e.g., dicyclohexylamine, alkylamines such as t-butylamine and t-amylamine, substituted alkylamines, aryl-alkylamines such as benzylamine, dialkylamines, substituted dialkylamines such as N-methyl glucamine (especially, N-methyl-D-glucamine), trialkylamines, and substituted trialkylamines), and salts with amino acids such as arginine, lysine and so forth. The basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aryl-alkyl halides (e.g. benzyl and phenethyl bromides), and others.

Prodrugs and solvates of the inventive compounds are also contemplated herein. The term "prodrug", as employed herein, denotes a compound which, upon administration to a subject, undergoes chemical conversion by metabolic or chemical processes to yield a compound of the formula I or II, or a salt and/or solvate thereof. See H. Bundgaard, "Drugs of the Future", 16 (5), 443–458 (1991); and H. Bundgaard (Ed), "Design of Prodrugs" 1985 Elsevier (Amsterdam), both incorporated herein by reference. Solvates of the compounds of the formulae I and II are preferably hydrates.

All stereoisomers of the present compounds are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

Methods for the Preparation of Compounds of the Formula I

The compounds of the formula I of the present invention may be prepared as illustrated in the following Reaction Scheme 1.

Reaction Scheme 1
Preparation of Compounds of the Formula I

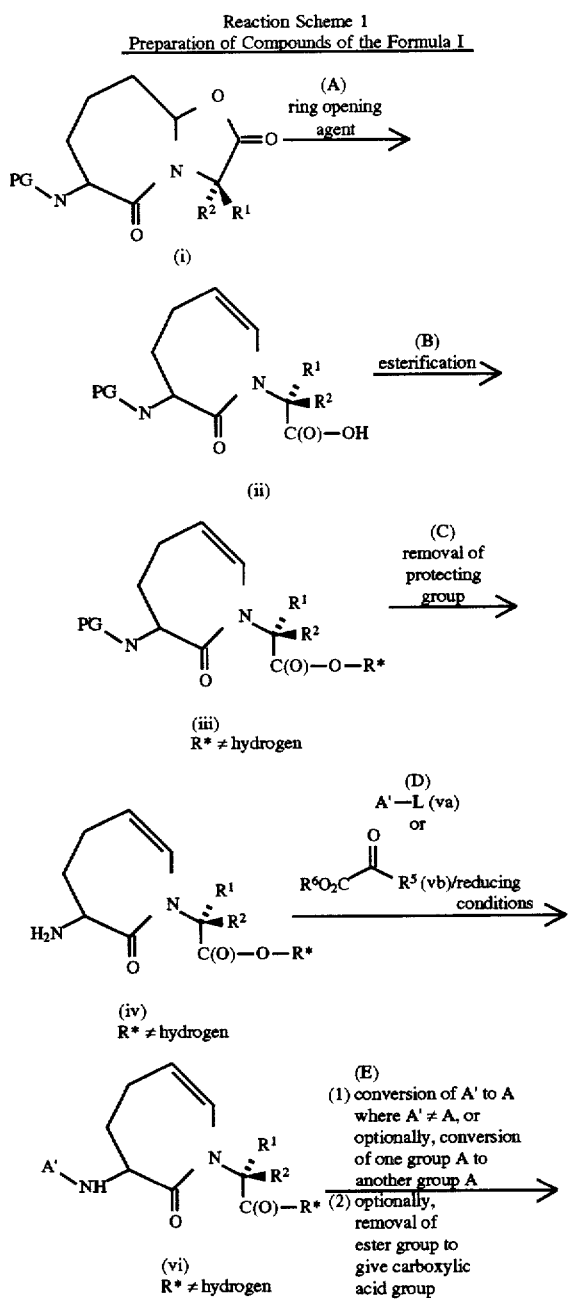

-continued
Reaction Scheme 1
Preparation of Compounds of the Formula I

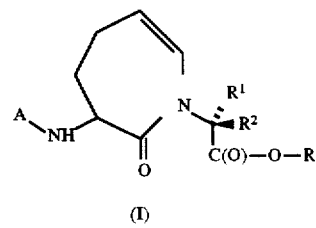

(I)

In step A of Reaction Scheme 1, the starting compound i is contacted with a ring opening agent to yield the unsaturated azepinone ii, preferably in a solvent such as methylene chloride. Exemplary ring opening agents include use of a Lewis acid (such as $SnCl_4$) and a Lewis base (such as triethylamine or trimethylaluminum). The ring opening agent is preferably trimethylsilyliodide followed by a tertiary amine base. The starting compound of the formula i may be prepared as described in or analogous to European Patent Application 599,444, incorporated by reference herein, or as described in or analogous to the Examples below. As used herein, "PG-N-" denotes a protected nitrogen atom. Exemplary groups PG-N- include those where the nitrogen is protected by a monovalent protecting group (especially, where PG-N- is benzyloxycarbonyl-NH- or tert-butoxycarbonyl-NH-), or, preferably, those where the nitrogen is protected by a divalent protecting group forming, together with the nitrogen, a ring (especially, where PG-N- is phthalimido).

In step B, the unsaturated azepinone ii is esterified, for example, by known methods for the esterification of a carboxylic acid group, to form the azepinone ester iii. An exemplary method for the preparation of an azepinone ester iii comprises contacting the unsaturated azepinone ii with ethereal diazomethane in methanol, or with methyliodide and base in a solvent, to provide the methyl ester. As used herein, R* denotes a group R as defined above, other than hydrogen, or any suitable acid protecting group, such as methyl, ethyl, t-butyl or benzyl.

The protecting group of the group PG-N- of the azepinone ester iii is removed in step C to yield the amino azepinone iv. The method employed may, for example, be any known method suitable for the removal of the particular protecting group present, for example, treatment with hydrazine monohydrate (in a solvent such as methanol) when PG-N- is phthalimido; treatment with iodotrimethylsilane when PG-N- is benzyloxycarbonyl-NH-; or treatment with hydrochloric acid in dioxane or other strong acid such as trimethylsilyliodide when PG-N- is t-butoxycarbonyl-NH-.

In step D, the amino azepinone iv is coupled with the compound va, A'-L, where L is a leaving group and A' is either a group A as described herein or a group A as described herein in which one or more groups are protected, to provide the compound vi. Preferred L groups are hydroxyl, halo (e.g., chloro), triflate ($-OSO_2CF_3$), or tolylsulfonoxy; preferred groups A' are

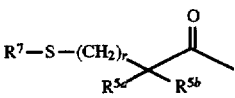

(especially, where $R^7$ is $R^8$—C(O)—, and L is hydroxyl),

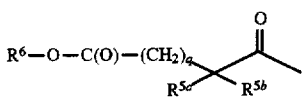

(especially, where $R^6$ is other than hydrogen, and L is hydroxyl),

(especially, where $R^6$ is other than hydrogen, and L is halo), or

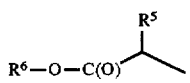

(especially, where $R^6$ is other than hydrogen, and L is triflate). Alternatively, to prepare a compound vi where A is $R^6O_2C$—CH($R^5$)—, the amino azepine iv may be contacted with a compound vb, $R^6O_2C$—C(O)—$R^5$, under reducing conditions.

Step D is preferably performed in an organic solvent such as methylene chloride. The above coupling is preferably conducted in the presence of a coupling reagent, for example, 1-ethyl-3-(3-dimethylamino-propyl) carbodiimide, dicyclohexylcarbodiimide, benzotriazol-1-yloxytris(dimethylamino)phosphonium hexafluorophosphate (especially, in the presence of a tertiary amine), or carbonyldiimidazole where the leaving group L is a hydroxyl group forming part of a carboxylic acid moiety. Where A'-L contains a carboxylic acid group, it can be converted to an activated form prior to coupling, such as to an acid chloride, mixed anhydride, symmetrical anhydride, activated ester, etc.

Compounds of the formula va may be prepared by methods described in the literature. See, for example, Ondetti et al. U.S. Pat. Nos. 4,105,776 and 4,339,600, Haslanger et al. U.S. Pat. No. 4,801,609, Delaney et al. U.S. Pat. No. 4,722,810, European Patent Application No. 629,627 etc. describing methods for the preparation of compounds of the formula

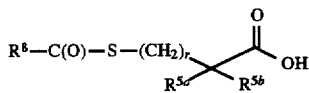

which may be used in the preparation of compounds of the formulae I and II where A is

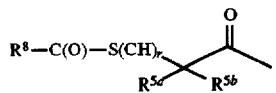

See, for example, Warshawsky et al., European Patent Application Nos. 534,396 and 534,492 describing methods for the preparation of compounds of the formula

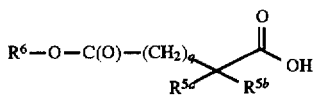

which may be used in the preparation of compounds of the formulae I and II where A is

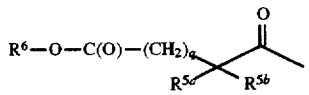

See, for example, Karanewsky et al. U.S. Pat. Nos. 4,432,971 and 4,432,972 and Karanewsky U.S. Pat. No. 4,460,579 describing methods for the preparation of phosphonochloridates of the formula

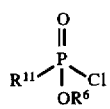

which may be used in the preparation of compounds of the formulae I and II where A is

See, for example, Attwood, M. R., Hassall, C. H., Krohn, A., Lawton, G., Redshaw, S., *J. Chem. Soc. Perkin I*, p. 1011 (1986) describing methods for the preparation of compounds of the formula $R^6$—O—C(O)—CH($R^5$)—(triflate) which may be used in the preparation of compounds of the formulae I and II where A is $R^6$—O—C(O)—CH($R^5$)—.

The keto acids and esters of the formula vb are described in the literature. See, for example, Ruyle U.S. Pat. No. 4,584,294 and Parsons et al. U.S. Pat. No. 4,873,235.

A compound of the formula vi where A' is not a group A may be converted to a compound of the formula I in step E(1) by removal of the protecting group(s) from A' such as by known methods. Optionally, one group A may be converted to a different group A in step E(1). For example:

a compound of the formula vi having a group A containing, as $R^7$, the group $R^8$—c(o)— (e.g., acetyl-S- or benzoyl-S-) may be contacted with an alkali metal hydroxide such as methanolic sodium hydroxide followed by contact with an aqueous acid such as HCl or $KHSO_4$ to yield the corresponding compound where $R^7$ is hydrogen;

a compound of the formula vi where $R^7$ is hydrogen can be acylated with an acyl halide of the formula $R^8$—C(O)—halo where halo is F, Cl or Br, or acylated with an anhydride of the formula $R^8$—C(O)—O—C(O)—$R^8$, to give the corresponding compound where $R^7$ is $R^8$—C(O);

a compound of the formula vi where $R^7$ is $R^{12}$—S— and $R^{12}$ is alkyl, substituted alkyl, cycloalkyl—$(CH_2)_p$—, aryl—$(CH_2)_p$, substituted aryl—$(CH_2)_p$, or heteroaryl—$(CH_2)_p$ may be prepared by reacting the corresponding compound where $R^7$ is hydrogen with a sulfonyl compound of the formula $H_3C$—$SO_2$—S—$R^{12}$ in an aqueous alcohol solvent. The compounds of the formula $H_3C$—$SO_2$—S—$R^{12}$ are known in the literature or can be prepared by known methods (see, for example, Smith et al., Biochemistry, 14, p. 766–771 (1975));

a compound of the formula vi where $R^7$ is HS—may be prepared by reacting the corresponding compound where $R^7$ is hydrogen with $H_3C—SO_2—S—C(phenyl)_3$ or $H_3C—SO_2—S—Si(alkyl)_3$, followed by removal of the triphenylmethyl or trialkylsilyl group under acidic conditions;

symmetrical disulfides may be prepared by direct oxidation of a compound of the formula vi where $R^7$ is hydrogen with iodine according to known procedures (see, for example, Ondetti et al. U.S. Pat. No. 4,105,776);

a compound of the formula vi where A is

and $R^6$ is other than hydrogen may be hydrogenated to yield the corresponding compound where $R^6$ is hydrogen; and a compound where R or $R^6$ is —$CH(R^8)$—O—$C(O)$—$R^9$ or

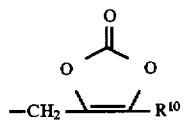

may be prepared by treating the corresponding compound where R or $R^6$ is hydrogen with a compound L—$CH(R^8)$—O—$C(O)$—$R^9$ or

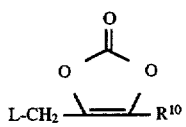

where L is a leaving group as defined above such as chloro, bromo, or tolylsulfonyloxy. Where a single such group R or $R^6$ is desired, group(s) other than the group to undergo reaction are suitably protected.

In step E(2), where a compound of the formula I is desired in which R is hydrogen, the ester group of the compound vi may be hydrolyzed by known methods to yield a carboxylic acid group, such as by contact with an alkali metal hydroxide such as methanolic sodium hydroxide followed by contact with an aqueous acid such as HCl or $KHSO_4$ where R* is alkyl, or by hydrogenation where R* is benzyl. Different esters having the group —$C(O)$—O—R where R is not hydrogen may be prepared, for example, by esterifying the carboxylic acid group formed in step E(2) by known methods to yield a compound having the desired group R.

Either of steps E(1) or E(2) may precede the other, or these steps may be conducted simultaneously, such as where the same reagents providing deprotection also provide hydrolysis. Thus, a compound containing a carboxyl group in place of the group —$C(O)$—O—R*, otherwise corresponding to formula vi, may be employed as appropriate in place of the formula vi compound in step E(1) as described above.

Methods for the Preparation of Compounds of the Formula II

The compounds of the formula II of the present invention may be prepared as illustrated in the following Reaction Scheme 2.

Reaction Scheme 2
Preparation of Compounds of the Formula II

Method (a)

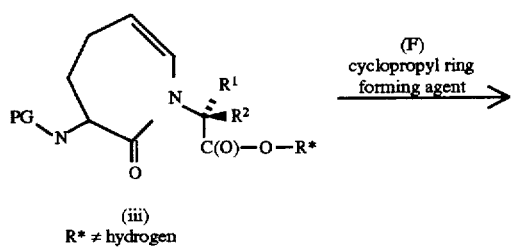

(iii)
R* ≠ hydrogen

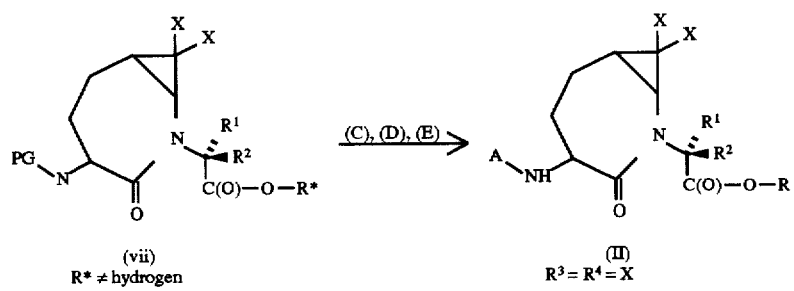

(vii)                    (II)
R* ≠ hydrogen        $R^3 = R^4 = X$

-continued
Reaction Scheme 2
Preparation of Compounds of the Formula II
Method (b)
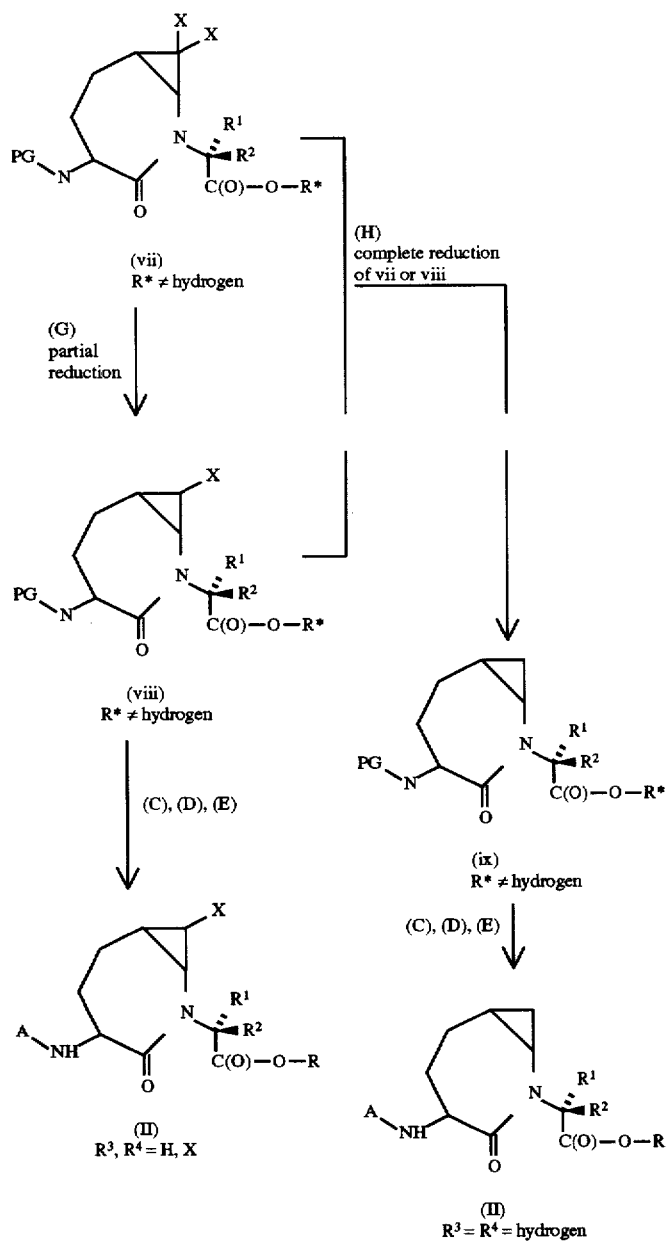

-continued
Reaction Scheme 2
Preparation of Compounds of the Formula II
Method (c)
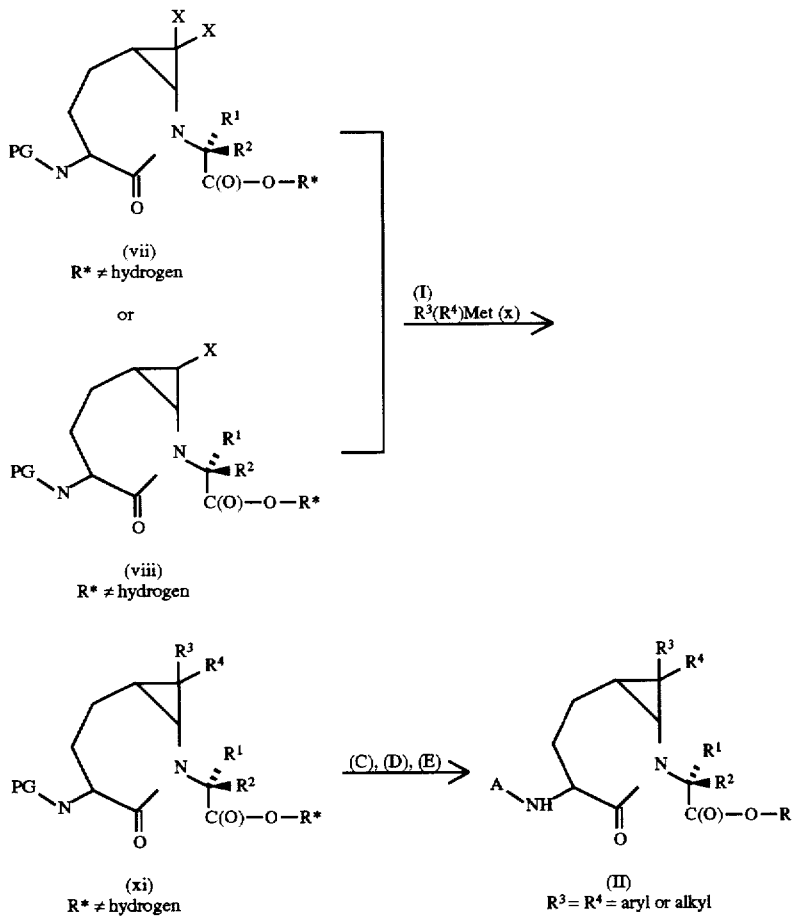
Method (d)
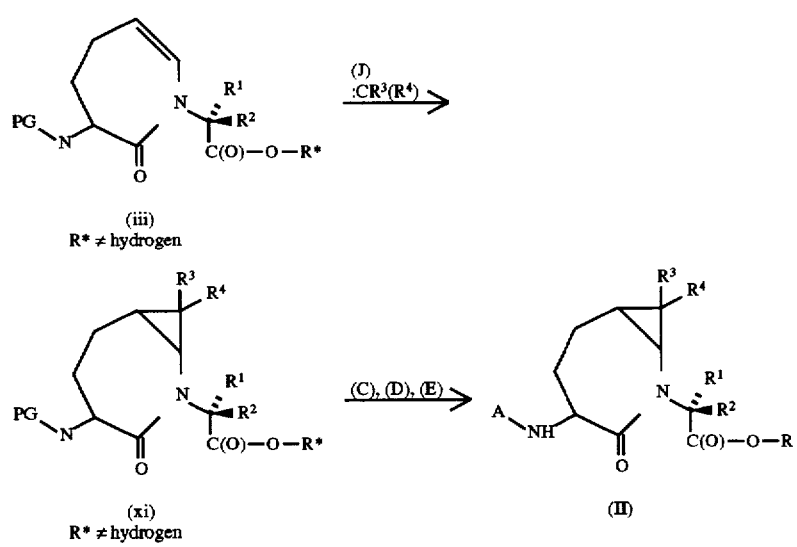
Reaction Scheme 2 describes four Methods (a, b, c and d) for the preparation of compounds of the formula II.
Method a illustrates preparation of compounds of the formula II where $R^3$ and $R^4$ are halo (halo is denoted by "X"

herein), especially, chloro or bromo. In this method, a compound of the formula iii (prepared in Reaction Scheme 1) is contacted, in step F, with a cyclopropyl ring forming agent such as phenyl(trihalomethyl)mercury (i.e., Ph(CX$_3$)Hg) to yield the dihalo azepinone vii. The dihalo azepinone vii obtained may be modified by use of steps C, D and E described in Reaction Scheme 1 above to obtain a compound of the formula II where R$^3$=R$^4$=X.

In Method b, a dihalo azepinone vii may be partially reduced as shown in step G to form a monohalo azepinone viii. Partial reduction is preferably conducted by use of a combination of tributyltinhydride (i.e., (n-Bu)$_3$SnH) or tristrimethylsilylsilane (i.e., (TMS)$_3$SiH) and 2,2'-azobisisobutyronitrile (i.e., AIBN), followed by quenching to minimize or eliminate complete reduction products. The monohalo azepinone viii obtained may be modified by use of steps C, D and E described in Reaction Scheme 1 above to form a compound of the formula II where one of R$^3$ and R$^4$ is hydrogen and the other is halo. Alternatively, the dihalo azepinone vii, or the monohalo azepinone viii, may be completely reduced to form azepinone ix as shown in step H, followed by use of steps C, D and E as described in Reaction Scheme 1 above to obtain a compound of the formula II where both R$^3$ and R$^4$ are hydrogen. Complete reduction is preferably achieved by use of a combination of (n-Bu)$_3$SnH or (TMS)$_3$SiH and AIBN, and by allowing the reaction to proceed sufficiently to produce completely reduced compounds. Most preferably, in either step G or step H, both (n-Bu)$_3$SnH and (TMS)$_3$SiH are employed in combination with AIBN.

Method c illustrates preparation of compounds of the formula II where R$^3$ and R$^4$ may be alkyl or aryl. Either dihalo azepinone vii or monohalo azepinone viii is contacted, in Step I, with an organometallic compound x which is R$^3$(R$^4$)Met. In compound x, R$^3$ and R$^4$ are alkyl or aryl groups and "Met" is a metal such as copper (organocuprates are preferred compounds x). The compound xi obtained may be modified by use of steps C, D and E described in Reaction Scheme 1 above to obtain a compound of the formula II. Compounds of the formula x may be prepared by methods such as those described in Lipshutz: Lipshutz, B. H. et al., "Organocopper Reagents: Substitutions, Conjugate Additions, Carbo/Metallocuprations, and Other Reactions" in Organic Reactions, Volume 41, pp. 135–590, J. Wiley & Sons (1992).

Method d illustrates another route for the preparation of compounds of the formula II, where, in step J, an azepinone ester iii is contacted with a carbene or carbene equivalent, that is, a reagent providing the entity :CR$^3$(R$^4$) where R$^3$ and R$^4$ may be hydrogen, alkyl, aryl or —C(O)—OR where R is as defined above. Exemplary carbenes or carbene equivalents include CH$_2$N$_2$, CH$_2$I$_2$, R$^3$—CHI$_2$, N$_2$CHCOR$^3$, N$_2$(CO$_2$R$^3$)$_2$, R$^3$—CO—R$^4$, Br$_2$CF$_2$, aryl—CCl$_3$, (CH$_3$)$_3$Si—CH$_2$—CO—CH$_2$—O—C(O)—CH$_3$, and Cl(F)$_2$CCO$_2$Na. The compound xi obtained may be converted to a compound of the formula II by the use of steps C, D and E as described in Reaction Scheme 1 above.

The compounds of the formulae I and II can contain asymmetric centers. While the optically pure form of these compounds is preferred, all stereoisomeric forms are within the scope of this invention. The above described processes can utilize as starting materials, and can prepare as products, compounds in any stereoisomeric form such as optically pure compounds, racemates, enantiomers, or diastereomers. If desired, when diastereomeric compounds are prepared, they can be separated, for example, by conventional chromatographic or fractional crystallization methods; when racemates are prepared, they can be separated, for example, by conventional methods such as salt formation with an optically active reagent and separation of the diastereomers formed, or by chiral column chromatography.

Suitable salts, especially pharmaceutically acceptable salts, may be employed or prepared by the methods described herein. Preferred salts for this purpose are basic salts, especially, alkali metal salts such as sodium and potassium, alkaline earth metal salts such as calcium and magnesium, salts derived from amino acids such as arginine, lysine, etc. and salts derived from amines such as alkylamines, e.g. t-butylamine, t-amylamine, etc., substituted alkylamines, aryl-alkylamines e.g. benzylamine, dialkylamines, substituted dialkylamines, e.g. N-methyl glucamine, trialkylamines, substituted trialkylamines, and quaternary ammonium salts. These salts can be obtained, for example, by reacting the acid form of the compound with a base supplying the desired ion in an organic medium in which the salt precipitates, or in aqueous medium and then lyophilizing.

Preferred Compounds

Preferred compounds of this invention are those having one or more (most preferably, all) of the following preferred substituent definitions:

A is

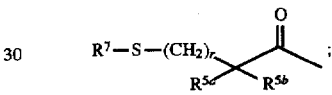

R$^1$ and R$^2$ are each independently hydrogen, alkyl or aryl—(CH$_2$)$_p$—;

R is hydrogen or lower alkyl;

R$^3$ and R$^4$ are each independently hydrogen, halo or lower alkyl;

one of R$^{5a}$ and R$^{5b}$ is hydrogen and the other is alkyl, substituted alkyl or aryl-alkylene such as benzyl;

R$^7$ is hydrogen or R$^8$—c(o)— where R$^8$ is lower alkyl;

p is zero or an integer from 1 to 4; and r is zero or one.

Particularly preferred compounds are the following:

[αS-(αR*,2R*,3R*)]-3-[[2-(acetylthio)-1-oxo-3-phenylpropyl]amino]-2,3,4,5-tetrahydro-α-methyl-2-oxo-1H-azepine-1-acetic acid, methyl ester;

[αS-(αR*,2R*,3R*)]-2,3,4,5-tetrahydro-3-[(2-mercapto-1-oxo-3-phenylpropyl)amino]-α-methyl-2-oxo-1H-azepine-1-acetic acid;

[S-(R*,R*)]-3-[[2-(acetylthio)-1-oxo-3-phenylpropyl]amino]-2,3,4,5-tetrahydro-2-oxo-1H-azepine-1-acetic acid, methyl ester;

[S-(R*,R*)]-2,3,4,5-tetrahydro-3-[(2-mercapto-1-oxo-3-phenylpropyl)amino]-2-oxo-1H-azepine-1-acetic acid;

[αS-(αR*,2R*,3R*)]-3-[[2-(acetylthio)-1-oxo-3-phenylpropyl]amino]-2,3,4,5-tetrahydro-α-(1-methylethyl)-2-oxo-1H-azepine-1-acetic acid, methyl ester;

[αS-(αR*,2R*,3R*)]-2,3,4,5-tetrahydro-3-[(2-mercapto-1-oxo-3-phenylpropyl)amino]-α-(1-methylethyl)-2-oxo-1H-azepine-1-acetic acid;

[1R-[1α, 4β(S*), 7α]]-4-[[2-(acetylthio)-1-oxo-3-phenylpropyl ]amino]-3-oxo-2-azabicyclo [5.1.0] octane-2-acetic acid, methyl ester;

[1S-[1α, 4α(R*),7α]]-4-[[2-(acetylthio)-1-oxo-3-phenylpropyl ]amino]-3-oxo-2-azabicyclo [5.1.0] octane-2-acetic acid, methyl ester;

[1R-[1α, 4β(S*), 7α]]-4-[(2-mercapto-1-oxo-3-phenylpropyl) amino]-3-oxo-2-azabicyclo[5.1.0] octane-2-acetic acid; and

[1S-[1α, 4α(R*),7α]]-4-[(2-mercapto-1-oxo-3-phenylpropyl) amino]-3-oxo-2-azabicyclo[5.1.0] octane-2-acetic acid.

Preferred Methods of Use

The compounds of the formulae I and II where A is

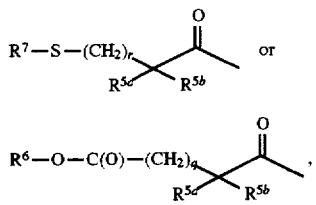

and pharmaceutically acceptable salts thereof, are dual inhibitors possessing the ability to inhibit both angiotensin converting enzyme (ACE) and neutral endopeptidase (NEP). The compounds of the formulae I and II where A is

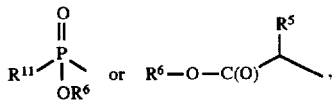

and pharmaceutically acceptable salts thereof, are selective inhibitors possessing the ability to inhibit the angiotensin converting enzyme.

The compounds of formulae I and II and their pharmaceutically acceptable salts are thus useful in the treatment of physiological conditions in which angiotensin converting enzyme inhibitors are useful. Such conditions include disease states characterized by abnormalities in blood pressure, intraocular pressure, and renin, including cardiovascular diseases (particularly, hypertension and congestive heart failure), glaucoma, and renal diseases (particularly, renal failure, diabetic nephropathy, and renal impairment following treatment with cyclosporine or other immunosuppressants). Other conditions in which angiotensin converting enzyme inhibitors have been reported to be useful include hepatic cirrhosis, inhibiting the progression of atherosclerosis, preventing or treating hypertensive or diabetic retinopathy, improving myocardial dysfunction during or following a myocardial infarction, and preventing restinosis after angioplasty.

The dual inhibitors are also useful in the treatment of physiological conditions in which neutral endopeptidase inhibitors are useful. Such conditions also include cardiovascular diseases (particularly hypertension), hyperaldosteronemia, renal diseases, glaucoma, as well as the relief of acute or chronic pain.

Thus, the compounds of the formulae I and II and their pharmaceutically acceptable salts are useful, for example, in reducing blood pressure, and the dual inhibitors are further useful for this purpose due to their diuresis and natriuresis properties. The dual inhibitors are particularly useful in the treatment of congestive heart failure.

The compounds of formulae I and II and pharmaceutically acceptable salts thereof can be administered for the aforementioned effects, such as in amounts similar to those employed previously for other angiotensin converting enzyme inhibitors. For example, the compounds of formulae I and II can be administered to a mammalian host such as man at from about 1 mg to about 100 mg per kg of body weight per day, preferably from about 1 mg to about 50 mg per kg of body weight per day. The compounds of formulae I and II and their pharmaceutically acceptable salts are preferably administered orally, but parenteral routes such as subcutaneous, intramuscular, and intravenous routes can also be employed as can topical routes of administration. The daily dose can be administered singly or can be divided, for example, into two to four doses administered throughout the day.

The inhibitors of formulae I and II and their pharmaceutically acceptable salts can be administered in combination with other classes of pharmaceutically active compounds, for example, in combination with a vasoactive peptide such as ANF 99-126, a diuretic, a calcium channel blocker, a potassium channel activator, a cholesterol reducing agent, a β-blocker, etc.

The inhibitors of formulae I and II, their pharmaceutically acceptable salts, and other pharmaceutically acceptable ingredients, can be formulated as pharmaceutical compositions for the above described uses. Exemplary compositions for oral administration include tablets, capsules, and elixirs; exemplary compositions for parenteral administration include sterile solutions and suspensions. Exemplary compositions for treating glaucoma also include topical compositions such as solutions, ointments, and solid inserts as described in U.S. Pat. No. 4,442,089. For example, about 10 to 500 mg of active ingredient may be compounded with a physiologically acceptable vehicle, carrier, excipient, binder, preservative, stabilizer, flavoring, etc., in a unit dose form as called for by accepted pharmaceutical practice.

The following Examples are provided to illustrate the invention, and are not intended to limit the scope of the present claims. Thin layer chromatography (TLC) was performed in silica gel unless otherwise stated. Abbreviations used in the following Examples have the meaning below, unless otherwise indicated.

ABBREVIATIONS

Ac= acetyl ($CH_3$—C(O)—)
AIBN= 2,2'-azobisisobutyronitrile
BOP reagent= benzotriazol-1- yloxytris(dimethylamino) phosphonium hexafluorophosphate (n-Bu)$_3$SnH= tributyltinhydride
DCHA= dicyclohexylamine
DiPEA= N,N-diisopropylethylamine
DMF= dimethylformamide
DMSO= dimethylsulfoxide
EDAC= 1-ethyl-3-(3-dimethylamino-propyl)carbodiimide
Et= ethyl
Et$_2$O= ethyl ether
EtOAc= ethyl acetate
HOAC= acetic acid
HOBT= hydroxybenztriazole
m.p.= melting point
Me= methyl
MeOH= methanol
PMA= phosphomolybdic acid
TEA= triethylamine
TFA= trifluoroacetic acid
TMSI= trimethylsilyliodide
(TMS)$_3$SiH= tristrimethylsilylsilane

EXAMPLE 1
Preparation of [αS-(αR*,2R*,3R*)]-3-[[2-(Acetylthio)-1-oxo-3-phenylpropyl]aminol-2,3,4 5-tetrahydro-α-methyl-2-oxo-1H-azepine-1-acetic acid, methyl ester

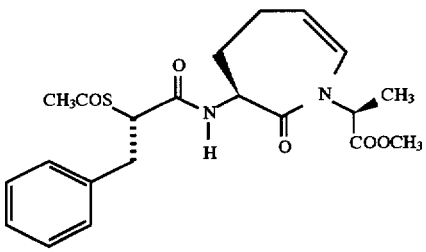

(A) (S)-1,3-Dihydro-α-(4-hydroxybutyl)-1,3-dioxo-2H-isoindole-2-acetic acid

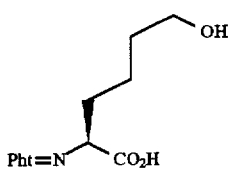

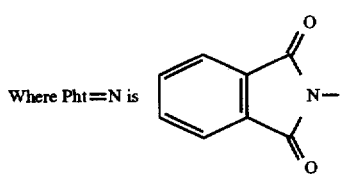

A solution of (+)-L-ε-hydroxynorleucine (1.030 g, 7.0 mmol):

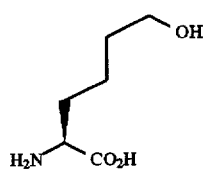

prepared by the method of Bodanszky, M. et al., J. Med. Chem., 21, 1030–1035 (1978), and Na₂CO₃ (745 mg, 7.0 mmol) in H₂O (12 mL) was treated with N-carbethoxyphthalimide (1.495 g, 7.0 mmol) and the mixture was stirred at room temperature for 2 hours. The solution was filtered, cooled to 0° C., and acidified with 6N HCl to afford a white precipitate. The solid was collected by filtration and dried in vacuo at 80° C. for 1 hour to give the title compound of this step as a pure acid (1.297 g, 67%). m.p.=162°–163° C. $[\alpha]_D$=–35.7° (c=1.3, MeOH); lit. $[\alpha]_D$= –36.3° (c=2, MeOH).

(B) (S)-N-[2-(1,3-Dihydro-1,3-dioxo-2H-isoindol-2-yl)-6-hydroxy-1-oxohexyl]-L-alanine, ethyl ester

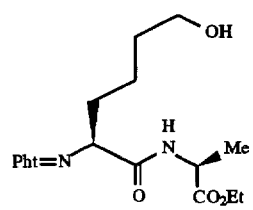

To a solution of L-alanine ethyl ester hydrochloride salt (1.865 g, 12.1 mmol) in DMF (27 mL) was added 4-methylmorpholine (1.70 mL, 1.56 g, 15.5 mmol). After stirring at room temperature for 5 minutes, the solution was treated with the title acid of step (A) (2.512 g, 9.06 mmol) and HOBT (1.258 g, 9.3 mmol), cooled to 0° C., and subsequently treated with EDAC (2.091 g, 10.9 mmol). The resulting mixture was stirred at 0° C. for 1 hour and at room temperature for 1.5 hours. The solution was partitioned between EtOAc and H₂O and the organic extract was washed successively with 0.5 N HCl, H₂O, 50% saturated NaHCO₃, and brine, then dried (Na₂SO₄), filtered and stripped to give the title compound of this step, essentially pure (3.111 g, 91%), as a white oily foam.
TLC R_f 0.23 (1:1-acetone:hexane)

(C) (S)-N-[2-(1,3-Dihydro-1,3-dioxo-2H-isoindol-2-yl)-5-formyl-1-oxopentyl]-L-alanine, ethyl ester

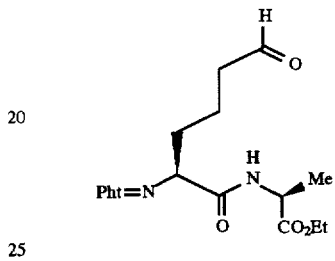

A –78° C. solution of oxalyl chloride (930 μL, 1.35 g, 10.7 mmol) in CH₂Cl₂ (30 mL) was treated dropwise with a solution of dry DMSO (1.50 mL, 1.65 g, 21.1 mmol) in CH₂Cl₂ (1.5 mL). After 10 minutes, a solution of the title alcohol of step (B) (3.088 g, 8.2 mmol) in CH₂Cl₂ (15 mL) was added. After an additional 15 minutes, the mixture was treated with TEA (6.8 mL), stirred at –78° C. for 5 minutes, then let warm to 0° C. The resulting white slurry was quenched with H₂O and extracted with EtOAc/Et₂O. The organic extract was washed with 1 N HCl and brine, then dried (Na₂SO₄), filtered and stripped. The residue was flash chromatographed (Merck SiO₂, 1:1-acetone:hexanes) to afford the title aldehyde of this step (2.860 g, 93%) as a near colorless oil.
TLC R_f 0.32 (1:1-acetone:hexanes)

(D) [3S -(3α, 6β, 9aα)]-6-(1,3-Dihydro-1,3-dioxo-2H-isoindol-2-yl)-7,8,9,9a-tetrahydro-3-methyloxazolo [3,2-a]azepine-2,5(3H,6H)-dione

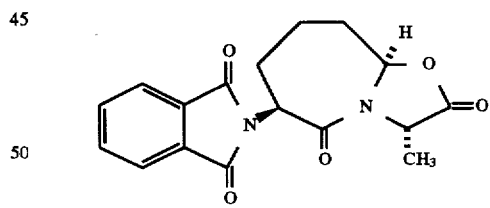

A mixture of the title aldehyde of step (C) (2.845 g, 7.6 mmol) and trifluoroacetic acid (22 mL) in CHCl₃ (85 mL) was refluxed for 48 hours, then stirred an additional 19 hours at room temperature. The volatiles were removed by rotary evaporation and the residue was redissolved in CH₂Cl₂ and triturated with EtOAc/Et₂O to afford an orange solid (1.48 g). The solid was recrystallized from CH₂Cl₂/EtOAC to give as pure the title bicycle of this step (985 mg, 39%) as white crystals. Both mother liquors were pooled, stripped, and flash chromatographed (Merck SiO₂, 15% acetone in CH₂Cl₂). The pure desired fractions were stripped and the residue was recrystallized from CH₂Cl₂/Et₂O to give additional product (689 mg, 28%). The total yield of product was 67%.

m.p.=250°–251° C. TLC $R_f$ 0.33 (1:1-acetone:hexanes) [α]$_D$=+103.1° (c=0.36, CHCl$_3$)

(E) [S-(R*,R*)]-3-(1,3-Dihydro-1,3-dioxo-2H-isoindol-2-yl)-2,3,4,5-tetrahydro-α-methyl-2-oxo-1H-azepine1-acetic acid

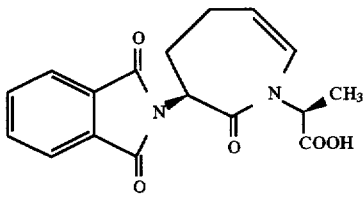

A solution of the title compound of step (D) (600 mg, 1.83 mmoles) in dry dichloromethane (9.0 ml) was treated with trimethylsilyliodide (0.65 ml, 2.5 eq) and stirred at room temperature for 5.0 hours. The solution was treated with DiPEA (1.85 ml, 10.6 mmoles), stirred at room temperature for 1.0 hour then diluted with EtOAc (55 ml). The organic solution was washed with 1.0 N HCl containing some NaHSO$_3$ and the aqueous phase was re-extracted with EtOAc. The combined organic extracts were washed with additional 1.0 N HCl containing some NaHSO$_3$ and H$_2$O, then extracted with saturated NaHCO$_3$ (3×22 ml). The combined bicarbonate extracts were acidified with 10% HCl (44 ml), extracted with EtOAc (2×90 ml) and the organic solutions were washed with brine, dried (anhydrous Na$_2$SO$_4$), filtered, evaporated to dryness and dried in vacuo.

The crude product mixture was chromatographed on a silica gel column (Merck), eluting the column with EtOAc and EtOAc:HOAc (100:1). The desired fractions were combined, evaporated to dryness, evaporated from toluene (2×50 ml), stripped to dryness and dried in vacuo to give the title compound of this step (432 mg, 71.9%) as a white solid with consistent $^1$H-NMR and $^{13}$C-NMR spectral data.

TLC: $R_f$ 0.70 (Silica gel; EtOAc:HOAc- 95:5; UV) m.p.= 167–169° C.

(F) [S-(R*,R*)]-3-(1,3-Dihydro-1,3-dioxo-2H-isoindol-2-yl)-2,3,4,5-tetrahydro-α-methyl-2-oxo-1H-azepine-1-acetic acid, methyl ester

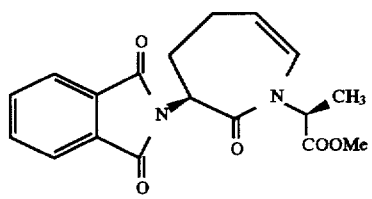

A solution of the title compound of step (E) (394 mg, 1.2 mmoles) in dry methanol (5.0 ml) was cooled to 0° C. (ice-salt bath), treated with excess CH$_2$N$_2$ in Et$_2$O (20 ml) and stirred at 0° C. for 10 minutes under argon. The reaction mixture was quenched with HOAc (0.3 ml), evaporated to dryness, evaporated once from toluene and dried in vacuo. The crude product was triturated with Et$_2$O:Hexane (1:5–30 ml), filtered, and dried in vacuo to give the title compound of this step as a white foam (412.2 mg, 100% crude yield) with consistent $^1$H-NMR and $^{13}$C-NMR spectral data.

TLC: $R_f$ 0.67 (Silica gel; EtOAc:Hexane-4:1; UV)

(G) [S-(R*,R*)]-3-Amino-2,3,4,5-tetrahydro-α-methyl-2-oxo1H-azepine- 1-acetic acid, methyl ester

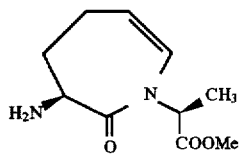

A solution of the title compound of step (F) (382 mg, 1.12 mmoles) in CH$_3$OH (15 ml) was treated with NH$_2$NH$_2$·H$_2$O (0.11 ml, 2.1 eq) and stirred at room temperature for 24 hours under argon. The reaction mixture was diluted with Et$_2$O (56 ml) and filtered, washing the solids well with Et$_2$O (4×10 ml). The clear filtrate was evaporated to dryness and the solids formed were triturated with CH$_2$Cl$_2$ (90 ml) and filtered, washing the solids well with CH$_2$Cl$_2$ (4×10 ml). The combined organic extracts were washed with brine (15 ml), dried (anhydrous Na$_2$SO$_4$), filtered, evaporated to dryness and dried in vacuo to give the title compound of this step as a syrup (250 mg, 100% crude yield) with consistent $^1$H-NMR and $^{13}$C-NMR spectral data.

TLC: $R_f$ 0.10 (Silica gel; EtOAc:MeOH:HOAc- 8:1:1; UV, PMA).

(H) [αS-(αR*,2R*,3R*)]-3-[[2-(Acetylthio)-1-oxo-3-phenylpropyl]amino]-2,3,4,5-tetrahydro-α-methyl-2-oxo-1H-azepine-1-acetic acid, methyl ester The DCHA salt of (S)-2-acetylthio-3-phenylpropionic acid (535 mg, 1.35 mmoles, 1.2 eq) was suspended in ethyl acetate (45 ml), washed with 5% KHSO$_4$ (5×6.5 ml) and brine, dried (anhydrous MgSO$_4$), filtered, evaporated to dryness and dried in vacuo.

The free acid obtained was dissolved in dry CH$_2$Cl$_2$ (10 ml), cooled to 0° C. (ice-salt bath) and treated sequentially with a solution of the title compound of step (G) (250 mg, 1.12 mmoles) in dry CH$_2$Cl$_2$ (5.0 ml), TEA (0.15 ml, 1.08 mmoles) and BOP reagent (494 mg, 1.12 mmoles). The reaction mixture was stirred at 0° C. for 1.0 hour and at room temperature for 2.5 hours under argon, stripped to dryness and the residual syrup re-dissolved in EtOAc (45 ml). The solution was washed with 0.5 N HCl, H$_2$O and brine, dried (anhydrous Na$_2$SO$_4$), filtered, evaporated to dryness and dried in vacuo. The crude product was chromatographed on a silica gel column (Merck), eluting the column with EtOAc:Hexane (1:3) to give the title compound of this Example as a syrup (384 mg, 81.9 %) with consistent $^1$H-NMR and $^{13}$C-NMR spectral data.

TLC: $R_f$ 0.53 (Silica gel; EtOAc:Hexane- 1:1; UV, PMA).

EXAMPLE 2

Preparation of [αS-(αR*,2R*,3R*)]-2,3,4,5-Tetrahydro-3-[(2-mercapto1-oxo-3phenylpropyl)amino]-α-methyl-2-oxo-1H-azepine-1-acetic acid

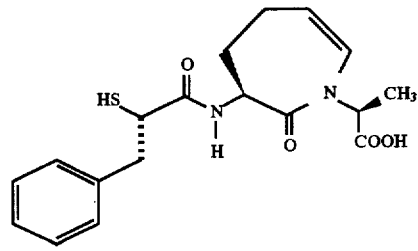

A solution of the title compound of step (H) of Example 1 (384 mg, 0.92 mmole) in CH$_3$OH (7.0 ml) was purged with argon for 30 minutes and treated dropwise with a solution of 1.0 N NaOH (3.68 ml, 4.0 eq, previously purged with argon for 30 minutes), maintaining the bubbling of argon throughout the addition and length of the reaction. The reaction mixture was stirred at room temperature for 1.0 hour then brought to pH 2.0 with 5% $KHSO_4$. The mixture was extracted with EtOAc (2×45 ml) and the combined organic extracts were washed with brine, dried (anhydrous $Na_2SO_4$), filtered, evaporated to dryness and dried in vacuo. The syrup obtained was evaporated from $CH_2Cl_2$:hexane (1:5; 20 ml) and hexane (3×20 ml) to give a solid foam which was triturated with $CH_2Cl_2$:hexane (1:5; 18 ml), hexane (20 ml) and pentane (20 ml), stirring with pentane for two hours. Drying in vacuo gave the title compound of this Example as a solid foam (284 mg, 59.0%) with consistent $^1$H-NMR, IR, MS and analytical data.

TLC: $R_f$ 0.68 (Silica gel; EtOAc:HOAc-95:5; UV). $[\alpha]_D$= −281.3° (c 0.60, $CH_3OH$) MS, $(M+H)^+$=363 HPLC: K'=6.17 (UV 220 nm) for peak at 14.34 min (99.2% S isomer); YMS S-3 ODS (C-18) 6×150 mm; 60% (10% $H_2O$- 90% MeOH- 0.2% $H_3PO_4$)/40% (90% $H_2O$- 10% MeOH- 0.2% $H_3PO_4$), isocratic; 1.5 ml/min flow rate. Anal. for $C_{18}H_{21}N_2O_4S$ · 0.28 $H_2O$ (Eff. Mol Wt.=367.564): Calc'd : C, 58.82; H, 6.19; N, 7.62; S, 8.72 Found : C, 58.82; H, 5.93; N, 7.35; S, 8.80

EXAMPLE 3

Preparation of [S-(R*,R*)]-3-[[2-(Acetylthio)1-oxo-3-phenylpropyl]amino]-2,3,4,5-tetrahydro-2-oxo-1H-azepine -1-acetic acid, methyl ester

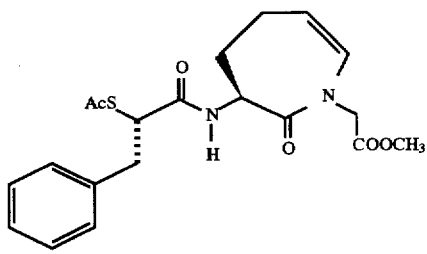

(A) (S)-N-[2-(1,3-Dihydro-1,3-dioxo-2H-isoindol-2-yl) -6-hydroxy1-oxohexyl]glycine, ethyl ester

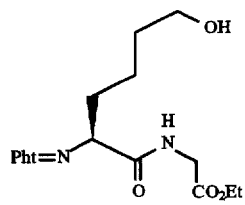

A slurry of glycine ethyl ester hydrochloride salt (2.718 g, 19.5 mmol) in DMF (36 mL) was treated with 4-methyl morpholine (2.60 mL, 2.39 g, 23.6 mmol) and stirred at room temperature for 5 minutes. The mixture was then treated with the title acid of Example 1, step (A) (4.500 g, 16.2 mmol) and HOBT (2.225 g, 16.5 mmol), cooled to 0° C., and then treated with EDAC (3.438 g, 17.9 mmol). After stirring at 0° C. for 1 hour and at room temperature for 2 hours, the mixture was partitioned between EtOAc and 0.5 N HCl and subsequently extracted three times with EtOAc. The pooled EtOAc extracts were washed in succession with $H_2O$, saturated $NaHCO_3$, and brine, then dried ($Na_2SO_4$), filtered and stripped to give the title compound of this step (5.770 g, 98%) as a colorless oil. The material was homogeneous to TLC.

TLC $R_f$ 0.34 (EtOAc)

(B) (S)-N-[2-(1,3-Dihydro-1,3-dioxo-2H-isoindol-2-yl) -5-formyl-1-oxopentyl]glycine, ethyl ester

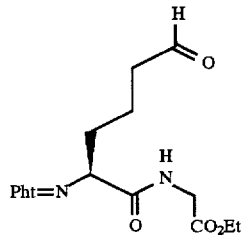

A −78° C. solution of oxalyl chloride (1.67 mL, 2.43 g, 19.1 mmol) in $CH_2Cl_2$ (50 mL) was treated dropwise with a solution of dry DMSO (2.70 mL, 2.97 g, 38.0 mmol) in $CH_2Cl_2$ (2 mL). After 15 minutes, a solution of the title alcohol of step (A) (5.770 g, 15.9 mmol) in $CH_2Cl_2$ (25 mL) was added. After an additional 15 minutes, the mixture was treated with TEA (10.0 mL), stirred at −78° C. for 5 minutes, then let warm to 0° C. The resulting mixture was washed with 1 N HCl and brine, then dried ($Na_2SO_4$), filtered and stripped. The residue was flash chromatographed (Merck $SiO_2$, 80:20-EtOAc:hexanes) to give as pure the title aldehyde of this step (5.170 g, 90%) as a colorless oil.

TLC $R_f$ 0.50 (EtOAc)

(C) (6S-trans)-6-(1,3-Dihydro-1,3-dioxo-2H-isoindol -2-yl)-7,8,9,9a-tetrahydrooxazolo [3,2-a]azepine-2, 5(3H,6H)-dione

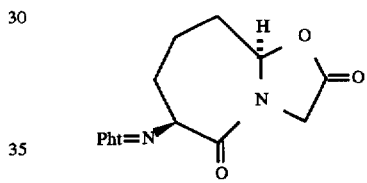

A solution of the title aldehyde of step (B) (5.160 g, 14.3 mmol) in TFA (40 mL) and $CHCl_3$ (160 mL) was refluxed under argon for 42 hours. The mixture was cooled to room temperature and neutralized with saturated aqueous $NaHCO_3$. The layers were separated and the aqueous layer was extracted with $CH_2Cl_2$. The pooled organic layers were washed with brine, dried ($Na_2SO_4$), and filtered through a short plug of silica gel, washing with 1:1-EtOAc:$CH_2Cl_2$. The filtrate was stripped to give a solid residue. The residue was slurried in $CH_2Cl_2$ and triturated with $Et_2O$ to give the title compound of this step (3.437 g, 76%) as a white solid. NMR analysis indicated the compound was isolated in 97% diastereomeric purity. NMR analysis (COSY & nOe) also indicated the stereochemistry as shown.

m.p.=234–240° C. TLC $R_f$ 0.51 (1:1-acetone:hexane)

(D) (S)-3-(1,3-Dihydro-1,3-dioxo-2H-isoindol -2-yl)-2,3, 4,5-tetrahydro-2-oxo -1H-azepine-1-acetic acid

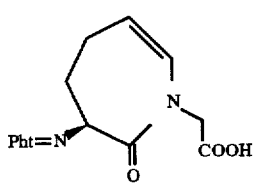

A solution of the compound prepared in step (C) (1.409 g, 4.48 mmoles) in dry $CH_2Cl_2$ (20 ml) was treated with TMSI (1.6 ml, 11.2 mmoles, 2.5 eq) and stirred at room temperature for 4.5 hours under argon. The mixture was treated with DiPEA (4.5 ml), stirred for an additional 50 minutes, then partitioned between EtOAc and 1.0 N HCl containing a small amount of sodium bisulfite. The aqueous washings were back-extracted with EtOAc and the combined organic extracts were washed with $H_2O$ and extracted with saturated $NaHCO_3$ (3x). The basic solutions were combined, made acidic with 10% HCl then extracted with EtOAc (2x). The organic extracts were washed with brine, dried (anhydrous $Na_2SO_4$), filtered, evaporated to dryness and dried in vacuo to give the title compound of this step as crystals. Trituration of the product with ether gave two crops of the title compound of this step (total=1.306 g, 93%).

TLC : $R_f$ 0.43 (Silica gel; EtOAc:HOAc- 95:5; UV, PMA), m.p.=197–198° C.

(E) (S)-3-(1,3-Dihydro-1,3-dioxo-2H-isoindol -2-yl)-2,3,4,5-tetrahydro-2-oxo -1H-azepine-1-acetic acid, methyl ester

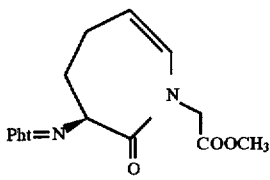

A suspension of the title compound of step (D) (400 mg, 1.27 mmoles) in methanol (8.0 ml) was cooled to 0° C. (ice-salt bath), treated with excess ethereal diazomethane and stirred at 0° C. for 30 minutes and then at room temperature for 1.0 hour. TLC of the mixture indicated that the reaction had gone to completion. The reaction mixture was quenched with glacial HOAc, evaporated to dryness and evaporated twice from toluene (25 ml). The precipitate obtained was triturated with $Et_2O$ (2×5.0 ml) to give the title compound of this step as a white solid (350 mg, 84%) with consistent $^1$H-NMR and $^{13}$C-NMR spectral data.

TLC : $R_f$ 0.68 (Silica gel; EtOAc:Hexane- 4:1; UV). m.p.=148–150° C. (F) (S) -3-Amino-2,3,4,5-tetrahydro-2-oxo-1H -azepine-1-acetic acid, methyl ester

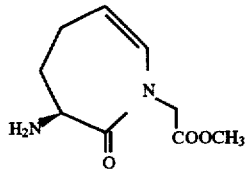

A solution of the title compound of step (E) (100 mg, 0.30 mmole) in methanol (4.0 ml) was treated with $NH_2NH_2 \cdot H_2O$ (30 µ, 2.1 eq) for 24 hours, diluted with $Et_2O$ (15 ml) and filtered, washing the solids with $Et_2O$ (10 ml). The clear filtrate was evaporated to dryness and the solid was triturated with $CH_2Cl_2$ (25 ml). The resulting suspension was filtered once more, washing the solid with $CH_2Cl_2$ (10 ml). The filtrate was washed with brine, dried (anhydrous $Na_2SO_4$), filtered, evaporated to dryness and dried in vacuo to give the title compound of this step as a syrup (48.1 mg, 87%) with consistent $^1$H-NMR and $^{13}$C-NMR spectral data.

TLC : $R_f$ 0.27 (Silica gel; EtOAc:MeOH:HOAc- 8:1:1; PMA, Ninhydrin).

(G) [S-(R*,R*)]-3-[[2-(Acetylthio)1-oxo-3-phenylpropyl]-amino]-2,3,4,5-tetrahydro -2-oxo1H-azepine-1-acetic acid, methyl ester The DCHA salt of (S)-2-acetylthio-3-phenylpropionic acid (502 mg, 1.27 mmoles) was suspended in ethyl acetate (40 ml), washed with 5% $KHSO_4$ (5×6.0 ml) and brine (6.0 ml), dried (anhydrous $MgSO_4$), filtered, evaporated to dryness and dried in vacuo.

The free acid obtained was dissolved in dry $CH_2Cl_2$ (9.0 ml), cooled to 0° C. (ice-salt bath) and treated sequentially with a solution of the title compound of step (F) (190 mg, 1.03 mmoles) in dry $CH_2Cl_2$ (3.0 ml), TEA (0.14 ml, 1.15 mmoles) and BOP reagent (462 mg, 1.04 mmoles). The reaction mixture was stirred at 0° C. for 1.0 hour and at room temperature for 2.5 hours under argon, then stripped to dryness. The residual syrup was dissolved in EtOAc (40 ml), washed with 0.5 N HCl, $H_2O$ and brine, dried (anhydrous $Na_2SO_4$), filtered, evaporated to dryness and dried in vacuo. The crude product mixture was chromatographed on a silica gel column (Merck), eluting the column with EtOAc:Hexane mixtures (1:3; 1:2) to give the title compound of this Example as a syrup (291.4 mg, 70%) with consistent $^1$H-NMR and $^{13}$C-NMR spectral data. TLC : $R_f$ 0.43 (Silica gel; EtOAc:Hexane- 1:1; UV).

EXAMPLE 4

Preparation of [S-(R*,R*)]-2,3,4,5-Tetrahydro-3-[(2-mercapto -1-oxo-3-Phenylpropyl)amino]-2-oxo-1H-azepine -1-acetic acid

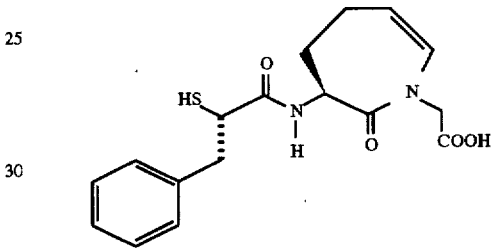

A solution of the title compound of step (G) of Example 3 (291 mg, 0.72 mmole) in methanol (5.0 ml) was purged with argon for 30 minutes, cooled to 0° C. (ice-salt bath) then treated with 1.0 N NaOH (2.9 ml, 4 eq; previously purged with argon for 30 minutes), maintaining the bubbling of argon throughout the addition and length of the reaction. The reaction mixture was stirred at 0° C. for 1.0 hour, brought to pH 2.0 with 5% $KHSO_4$, warmed up to room temperature and extracted with EtOAc (2×25 ml). The combined organic extracts were washed with brine, dried (anhydrous $Na_2SO_4$), filtered, evaporated to dryness and dried in vacuo. The syrup obtained was evaporated several times from hexane until a solid foam was obtained. This solid was triturated with $CH_2Cl_2$:Hexane (1:10- 55 ml), hexane (50 ml) and pentane (50 ml), stirring with pentane for 4.0 hours, then dried in vacuo to give the title compound of this Example as a solid foam (232.4 mg, 92.8%) with consistent analytical, IR, MS, $^1$H-NMR and $^{13}$C-NMR spectral data.

TLC : $R_f$ 0.52 (Silica gel; EtOAc:HOAc- 95:5; UV) $[\alpha]_D$=-216.4° (c0.68, $CH_3OH$) MS, $(M+H)^+$=349 HPLC : K'=1.92 (UV 220 nm) for peak at 5.846 min (97.3% S isomer); YMS S-3 ODS (C-18) 6×150 mm; 60% (10% $H_2O$-90% MeOH- 0.2% $H_3PO_4$)/40% (90% $H_2O$- 10% MeOH- 0.2% $H_3PO_4$), isocratic. Anal. for $C_{17}H_{20}N_2O_4S$: Calcld. : C, 58.60; H, 5.79; N, 8.04; S, 9.20 Found : C, 58.52; H, 5.88; N, 7.87; S, 8.97

EXAMPLE 5

Preparation of [αS-(αR*,2R*,3R*)]-3-[[2-(Acetylthio)-1-oxo-3-phenylpropyl]amino]-2,3,4,5-tetrahydro-α-(1-methylethyl)-2-oxo1H-azepine-1-acetic acid, methyl ester

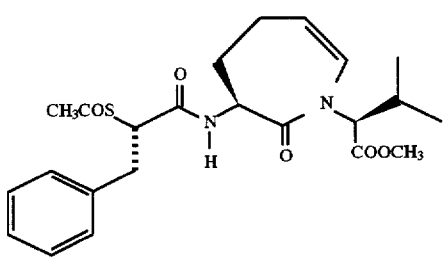

(A) (S)-N-[2-(1,3-Dihydro-1,3-dioxo-2H-isoindol-2-yl)-6-hydroxy-1-oxohexyl]-L-valine, methyl ester

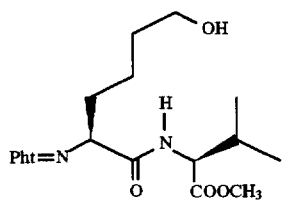

A solution of the hydrochloride salt of L-valine methyl ester (5.74 g, 34.3 mmoles) in dry dimethylformamide (76 ml) was treated with 4-methylmorpholine (4.8 ml, 43.8 mmoles) and stirred at room temperature under argon for 5 minutes. The mixture was then treated with HOBT·H₂O (3.56 g, 26.4 mmoles) and the title compound of Example 1, step (A) (7.11 g, 25.6 mmoles), cooled to 0° C. (ice-salt bath), and then treated with EDAC (5.92 g, 30.9 mmoles). The reaction mixture was stirred at 0° C. for 1.0 hour, at room temperature for 1.5 hours then partitioned between EtOAc (500 ml) and H₂O (200 ml). The aqueous phase was back-extracted with EtOAc (250 ml) and the combined organic extracts washed sequentially with H₂O (5×100 ml), 0.5 N HCl (80 ml) and brine (80 ml). The solution was dried (anhydrous Na₂SO₄), filtered, evaporated to dryness and dried in vacuo to give the title compound of this step as a white foam (10.14 g, 98.7%) with consistent ¹H-NMR and ¹³C-NMR spectral data. TLC : R_f 0.53 (Silica gel; Acetone:Hexane- 1:1; UV). [α]_D=+42.3° (c0.53, CHCl₃)

(B) (S)-N-[2-(1,3-Dihydro-1,3-dioxo-2H-isoindol-2-yl)-5-formyl-1-oxopentyl]-L-valine, methyl ester

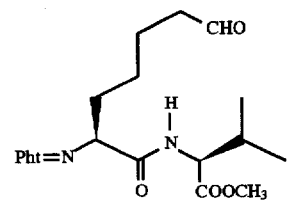

A solution of oxalyl chloride (2.83 ml, 32.4 mmoles) in dry CH₂Cl₂ (90 ml) was cooled to −78° C. (dry ice-acetone bath), treated with a solution of DMSO (4.56 ml, 64.1 mmoles) in dry CH₂Cl₂ (4.56 ml) and stirred at −78° C. for 10 minutes. The mixture was then treated with a solution of the title compound of step (A) (10.0 g, 24.9 mmoles) in dry CH₂Cl₂ (45 ml), stirred for 10 minutes, then treated with TEA (20.7 ml, 0.15 mole), stirred for an additional 5 minutes and warmed up to 0° C. The mixture was quenched with H₂O (50 ml) and extracted with EtOAc:Et₂O (17:3−2×200 ml). The whitish emulsion was washed with 1.0 N HCl (100 ml) and brine (100 ml), dried (anhydrous Na₂SO₄), filtered, evaporated to dryness and dried in vacuo. The crude product was chromatographed on a silica gel column (Merck), eluting the column with acetone:hexane to give the title compound of this step as a thick syrup (9.5 g, 95.8%) with consistent ¹H-NMR and ¹³C-NMR spectral data.

TLC : R_f 0.63 (Silica gel; acetone:hexane-1:1; UV) MS, (M+H)+=389.1726

(C) [3S-(3α,6β,9aα)-6-(1,3-Dihydro-1,3-dioxo-2H-isoindol-2-yl)-7,8,9,9a-tetrahydrooxazolo [3,2-a]azepine-2,5(3H,6H)-dione

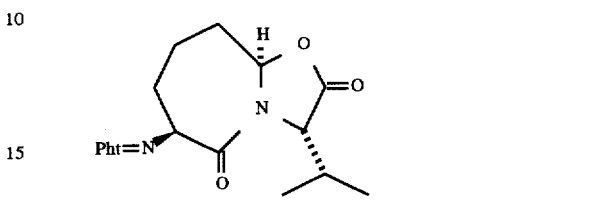

A solution of the title compound of step (B) (9.5 g, 23.8 mmoles) in CHCl₃ (2.4 L) was treated with TFA (69 ml, 0.90 mole), refluxed under argon for 19 days then stripped to dryness. The dark gold syrup was chromatographed on a silica gel column (Merck), eluting the column with CH₂Cl₂:acetone to give an off-white solid (5.74 g). The crude product was triturated with Et₂O (30 ml) and filtered, washing the white precipitates with a minimal amount of Et₂O (10 ml) to give the title compound of this step (4.034 g) with consistent ¹H-NMR and ¹³C-NMR spectral data.

TLC : R_f 0.77 (Silica gel; acetone:hexane1:1; UV). m.p.= 204–206° C. MS, (M+H)⁺=357 [α]_D=+93.5° (c0.88, CHCl₃) Anal. for C₁₉H₂₀N₂O₅ : Calc'd : C, 64.04; H, 5.66; N, 7.86 Found : C, 63.98; H, 5.61; N, 7.76

(D) [S-(R*,R*)]-3-(1,3-Dihydro-1,3-dioxo-2H-isoindol-2-yl)-2,3,4,5-tetrahydro-α-(1-methylethyl)-2-oxo-1H-azepine-1-acetic acid

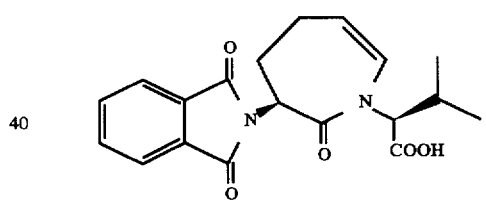

A solution of the title compound of step (C) (300 mg, 0.84 mmole) in dry dichloromethane (4.0 ml) was treated with TMSI (0.3 ml, 2.5 eq) and stirred at room temperature for 20 hours. The solution was treated with DiPEA (0.85 ml, 4.88 mmoles), stirred at room temperature for 1.0 hour, then diluted with EtOAc (40 ml). The organic solution was washed with 1.0 N HCl containing some NaHSO₃ and the aqueous phase was re-extracted with EtOAc. The combined organic extracts were washed with 1.0 N HCl containing NaHSO₃ and H₂O then extracted with saturated NaHCO₃ (3×20 ml). The combined bicarbonate extracts were acidified with 10% HCl (40 ml), extracted with EtOAc (2×60 ml) and the organic solutions were washed with brine, dried (anhydrous Na₂SO₄), filtered, evaporated to dryness and dried in vacuo.

The crude product mixture was chromatographed on a silica gel column (Merck), eluting the column with EtOAc and EtOAc:HOAc (100:1). The desired fractions were combined, evaporated to dryness, evaporated from toluene (2×100 ml), stripped to dryness and dried in vacuo to give the title compound of this step (235 mg, 78.3%) as a white foam with consistent ¹H-NMR and ¹³C-NMR spectral data.

TLC : R_f 0.72 (Silica gel; EtOAc:HOAc- 95:5; UV)

(E) [S-(R*,R*)]-3-(1,3-Dihydro-1,3-dioxo-2H-isoindol-2-yl)-2,3,4,5-tetrahydro-α(1-methylethyl)-2-oxo-1H-azepine-1-acetic acid, methyl ester

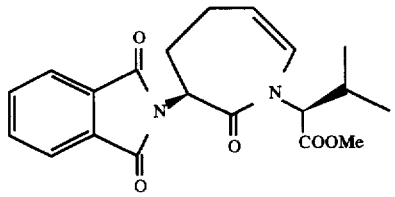

A solution of the title compound of step (D) (478 mg, 1.34 mmoles) in dry methanol (5.0 ml) was cooled to 0° C. (ice-salt bath), treated with excess $CH_2N_2$ in $Et_2O$ (20 ml) and stirred at 0° C. for 10 minutes under argon. The reaction mixture was quenched with HOAc, evaporated to dryness, evaporated once from toluene and dried in vacuo. The crude product was triturated with $Et_2O$:hexane (1:5-30 ml), filtered, and dried in vacuo to give the title compound of this step as a white solid (428 mg, 86.2%) with consistent $^1$H-NMR and $^{13}$C-NMR spectral data.

TLC : $R_f$ 0.78 (Silica gel; EtOAc:hexane-4:1; UV) m.p.= 164–165° C.

(F) [S-(R*,R*)]-3-Amino-2,3,4,5-tetrahydro-2-oxo1H-azepine-1-acetic acid, methyl ester

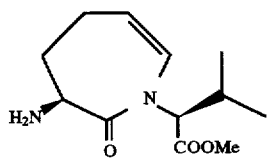

A solution of the title compound of step (E) (420 mg, 1.13 mmoles) in $CH_3OH$ (15 ml) was treated with $NH_2NH_2 \cdot H_2O$ (0.11 ml, 2.1 eq) and stirred at room temperature for 48 hours under argon. The reaction mixture was diluted with $Et_2O$ (50 ml) and filtered, washing the solids well with $Et_2O$ (4×10 ml). The clear filtrate was evaporated to dryness and the solids formed were triturated with $CH_2Cl_2$ (90 ml) and filtered, washing the solids well with $CH_2Cl_2$ (4×10 ml). The combined organic extracts were washed with brine (15 ml), dried (anhydrous $Na_2SO_4$), filtered, evaporated to dryness and dried in vacuo to give the title compound of this step as a cream-colored solid (275.7 mg, 100% crude yield) with consistent $^1$H-NMR and $^{13}$C-NMR spectral data.

TLC : $R_f$ 0.10 (Silica gel; EtOAc:MeOH:HOAc- 8:1:1; UV, PMA). m.p.=75–77° C. (G) [αS-(αR*,2R*,3R*)]-3-[[2-(Acetylthio) 1-oxo-3-phenylpropyl]amino]-2,3,4,5-tetrahydro -α-(1-methylethyl)-2-oxo-1H -azepine-1-acetic acid, methyl ester The DCHA salt of (S)-2-acetylthio-3-phenylpropionic acid (535 mg, 1.35 mmoles, 1.2 eq) was suspended in ethyl acetate (45 ml), washed with 5% $KHSO_4$ (5×6.5 ml) and brine (6.5 ml), dried (anhydrous $MgSO_4$), filtered, evaporated to dryness and dried in vacuo.

The free acid obtained was dissolved in dry $CH_2Cl_2$ (10 ml), cooled to 0° C. (ice-salt bath) and treated sequentially with a solution of the title compound of step (F) (275 mg, 1.13 mmoles) in dry $CH_2Cl_2$ (4.5 ml), TEA (0.15 ml, 1.08 mmoles) and BOP reagent (494 mg, 1.12 mmoles). The reaction mixture was stirred at 0° C. for 1.0 hour and at room temperature for 2.0 hours under argon, stripped to dryness and the residual syrup re-dissolved in EtOAc (45 ml). The solution was washed with 0.5 N HCl (2×7.0 ml), $H_2O$ (7.0 ml) and brine (7.0 ml), dried (anhydrous $Na_2SO_4$), filtered, evaporated to dryness and dried in vacuo. The crude product was chromatographed on a silica gel column (Merck), eluting the column with EtOAc:hexane (1:3) to give the title compound of this Example as a solid (406 mg, 80.6%) with consistent $^1$H-NMR and $^{13}$C-NMR spectral data.

TLC : $R_f$ 0.62 (Silica gel; EtOAc:hexane- 1:1; UV, PMA). m.p.=80–82° C.

EXAMPLE 6

Preparation of [αS- (αR*,2R*,3R*)]-2,3,4,5-Tetrahydro-3-[(2-mercapto-1-oxo-3-phenylpropyl)amino]-α-(1-methylethyl) -2-oxo-1H-azepine-1-acetic acid

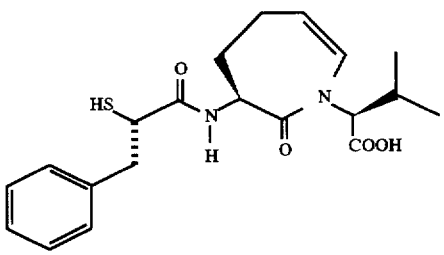

A solution of the title compound of step (G) of Example 5 (396.5 mg, 0.89 mmole) in $Ch_3OH$ (6.0 nl) was purged with argon for 30 minutes, cooled to 0° C. (ice-salt bath) and treated dropwise with a solution of 1.0 N NaOH (3.57 ml, 4.0 eq, previously purged with argon for 30 minutes), maintaining the bubbling of argon throughout the addition and length of the reaction. The reaction mixture was stirred at 0° C. for 1.0 hour, at room temperature for 4.0 hours, then brought to pH 2.0 with 5% $KHSO_4$. The mixture was extracted with EtOAc (2×45 ml) and the combined organic extracts were washed with brine (10 ml), dried (anhydrous $Na_2SO_4$), filtered, evaporated to dryness and dried in vacuo. The solid obtained was triturated twice with EtOAc:$Et_2O$ (1:3) to give the title compound of this Example as a white solid (205 mg, 59.0%) with consistent $^1$H-NMR, IR, MS and analytical data.

TLC: $R_f$ 0.82 (Silica gel; EtOAc:HOAc-95:5; UV). m.p.= 207–209° C. $[\alpha]_D$=–310.4° (c0.53, $CH_3OH$) MS, (M+H)$^+$= 391 HPLC : K'=6.17 (UV 220 nm) for peak at 14.34 min (99.2% S isomer); YMS S-3 ODS (C-18) 6×150 mm; 60%(10% $H_2O$- 90% MeOH- 0.2% $H_3PO_4$)/ 40% (90% $H_2O$- 10% MeOH- 0.2% $H_3PO_4$), isocratic; 1.5 mL/min flow rate. Anal. for $C_{20}H_{26}N_2O_4S \cdot 0.12\ H_2O$ (Eff Mol Wt=392.714): Calc'd : C, 61.17; H, 6.74; N, 7.13; S, 8.16 Found : C, 61.17; H, 6.78; N, 7.20; S, 8.11

EXAMPLE 7

Preparation of [1R-[1α,4β(S*),7α]]-4-[[2-(Acetylthio)-1-oxo-3-phenylpropyl]amino]-3-oxo-2-azabicyclo [5.1.0] octane-2-acetic acid, methyl ester (Isomer (7a))

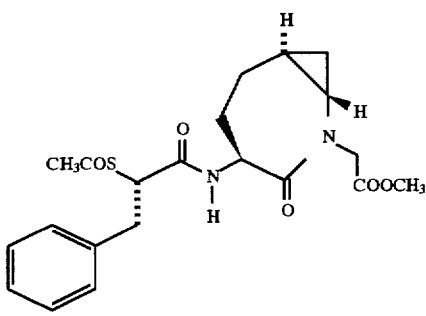

and

Preparation of [1S-[1α,4α(R*),7α]]-4-[[2-(acetylthio)-5 1-oxo-3-phenylpropyl]amino]-3-oxo-2-Azicyclo [5.1.0] octane-2-acetic acid, methyl ester (Isomer (7b))

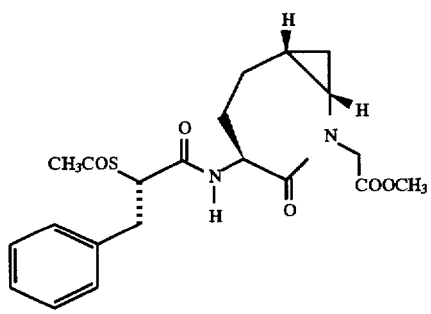

(A) [1S-(1α,4β,7α)]-8,8-Dibromo-4-(1,3-Dihydro-1,3-Dioxo-2H-Isoindol-2-yl)-3-oxo-2-azabicyclo [5.1.0]octane-2-acetic acid, methyl ester Isomer (a)

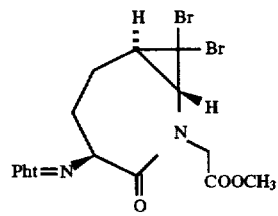

and [1R-(1α, 4α,7α)]-8,8-Dibromo-4- (1,3-dihydro-1,3-dioxo-2H-isoindol-2-yl)-3-oxo-2-azabicyclo [5.1.0]octane-2-acetic acid, methyl ester Isomer (b)

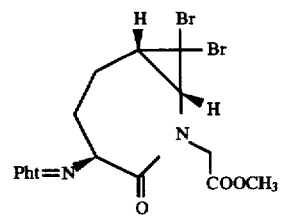

A mixture of the title compound of Example 3, step (E) (3.036 g, 9.66 mmoles) and phenyl-(tribromomethyl) mercury (7.51 g, 14.2 mmoles) in dry benzene (150 ml) was refluxed gently for 24 hours, treated with additional phenyl (tribromomethyl)mercury (7.51 g, 14.2 mmoles), and refluxed for another 40 hours under argon. The reaction mixture was diluted with $CH_2Cl_2$ (100 ml), filtered, and the clear filtrate evaporated to dryness. The residual solid was triturated with $CH_2Cl_2$ (3×100 ml), filtered and the clear filtrate evaporated to dryness. The syrup obtained was dissolved in EtOAc (200 ml), washed with 1.0 N HCl (2×25 ml) and brine (25 ml), dried (anhydrous $Na_2SO_4$), filtered, evaporated to dryness and dried in vacuo. The crude product mixture was chromatographed on a silica gel column (Merck), eluting the column with EtOAc:hexane mixtures to give Isomer (a) of the title compound of this step as a solid (3.08 g, 63.8%, m.p.=145–147° C.) with consistent $^1$H-NMR and $^{13}$C-NMR spectral data.

TLC: $R_f$ 0.47 (Silica gel; EtOAc:hexane-6:4; UV, $I_2$). Isomer (b) of the title compound of this step (450 mg), still containing traces of Isomer (a), was also isolated, bringing the total yield of both Isomers to 73.1%.

TLC: $R_f$ 0.43 (Silica gel; EtOAc:hexane-6:4; UV, $I_2$). m.p.=167–168° C.

(B) [1R-(1α,4β,7α)]-4-(1,3-Dihydro-1,3-dioxo-2H-isoindol -2-yl)-3-oxo-2-azabicyclo [5.1.0]octane-2-acetic acid, methyl ester

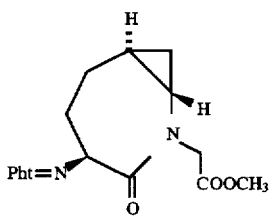

A solution of Isomer (a) of the title compound of step (A) (1.0 g, 2.1 mmoles) in dry toluene (50 ml) was purged with argon for 30 minutes, then treated with $(TMS)_3SiH$ (1.85 ml, 3 eq) and catalytic AIBN. The mixture was stirred at 55° C. (oil bath) under argon for 1.5 hours, treated with $(n-Bu)_3SnH$ (1.61 ml, 3 eq) and catalytic AIBN. Heating was continued for the next four days with the intermittent addition of catalytic AIBN (at 4, 16, 20, 24, and 48 hours). The reaction mixture was cooled, diluted with $CHCl_3$ (90 ml), stirred and filtered, washing the solids with $CHCl_3$ (3×45 ml). The combined organic extracts were washed with saturated $NaHCO_3$ (45 ml), 5% $Na_2S_2O_3$ (45 ml) and $H_2O$ (3×45 ml), dried (anhydrous $Na_2SO_4$), filtered, evaporated to dryness and dried in vacuo.

The crude product mixture was chromatographed on a silica gel column (Merck), eluting the column with $CH_2Cl_2$ followed by $CH_2Cl_2$:EtOAc (85:15). The crude product (600 mg, 56.6%) obtained was triturated with hexane (3×20 ml) to remove traces of $(n-Bu)_3SnH$, combined with an earlier batch of clean product (226 mg) and re-chromatographed on a silica gel column (Merck). Elution with EtOAc:hexane (1:2) gave the title compound of this step as a white solid (506 mg, m.p.=193–195° C.) with consistent $^1$H-NMR and $^{13}$C-NMR spectral data.

TLC: $R_f$ 0.37 (Silica gel; EtOAc:hexane- 1:1; UV).

(C) [1R-(1α,4β,7α)]-4-amino-3-oxo-2-azabicyclo [5.1.0] octane-2-acetic acid, methyl ester

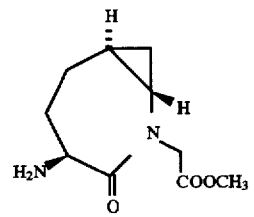

A solution of the title compound of step (B) (300 mg, 0.88 mmole) in $Ch_3OH$ (12 ml), was treated with $NH_2NH_2·H_2O$ (0.10 ml, 2.2 eq) and stirred at room temperature for 48 hours under argon. The reaction mixture was diluted with Et₂O (45 ml) and filtered through a millipore unit, washing the solids with Et₂O (30 ml). The filtrate was stripped to dryness, triturated with CH₂Cl₂ (70 ml) and filtered again. The filtrate and washings were washed with brine, dried (anhydrous Na₂SO₄), filtered, evaporated to dryness and dried in vacuo to give the title compound of this step as a syrup (178.5 mg, 95.6%) with consistent ¹H-NMR and ¹³C-NMR spectral data.

TLC: R_f 0.28 (Silica gel; EtOAc:MeOH- 10:1; UV).

(D) [1R-[1α, 4β(S*),7α]]-4-[[2-(acetylthio)-1-oxo-3-phenylpropyl]amino]-3-oxo-2-azabicyclo [5.1.0]octane-2-acetic acid, methyl ester (Isomer (7a))

The DCHA salt of (S)-2-acetylthio-3-phenylpropionic acid (398 mg, 0.98 mmole, 1.2 eq) was suspended in ethyl acetate (34 ml), washed with 5% KHSO₄ (5×5.0 ml) and brine (5.0 ml), dried (anhydrous MgSO₄), filtered, evaporated to dryness and dried in vacuo.

The free acid obtained was dissolved in dry CH₂Cl₂ (7.0 ml), cooled to 0° C. (ice-salt bath) and treated sequentially with a solution of the title compound of step (C) (178.5 mg, 0.84 mmole) in dry CH₂Cl₂ (5.0 ml), TEA (0.12 ml, 0.91 mmole) and BOP reagent (410 mg, 0.91 mmole). The reaction mixture was stirred at 0° C. for 1.0 hour and at room temperature for 2.0 hours under argon, then stripped to dryness. The residual syrup was re-dissolved in EtOAc (35 ml), washed with 0.5 N HCl, H₂O and brine, dried (anhydrous Na₂SO₄), filtered, evaporated to dryness and dried in vacuo. The crude product was chromatographed on a silica gel column (Merck), eluting the column with EtOAc:hexane mixtures (1:3; 1:1) to give the Isomer (7a) title compound of this Example as a syrup (307.6 mg, 87.5%) with consistent ¹H-NMR and ¹³C-NMR spectral data.

TLC: R_f 0.30 (Silica gel; EtOAc:hexane1:1; UV).

(E) [1S- [1α,4α(R*),7α]]-4-[[2- (acetylthio) -1-oxo-3-phenylpropyl]amino]-3-oxo-2-azabicyclo [5.1.0]octane-2-acetic acid, methyl ester (Isomer (7b))

Conducting steps (B) to (D) of this Example, using the Isomer (b) title compound of step (A) in place of Isomer (a), provides the Isomer (7b) title compound of this Example.

EXAMPLE 8

Preparation of [1R-[1α,4β(S*),7α]]-4- [(2-Mercapto1-oxo-3-phenylpropyl)amino]-3-oxo-2-azabicyclo [5.1.0]octane-2-acetic acid (Isomer (8a))

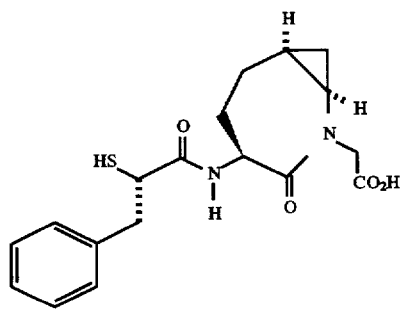

and

Preparation of [1S-[1α,4α(R*),7α]]-4-[(2-Mercapto-1-oxo-3-phenylpropyl)amino]-3-oxo-2-azabicyclo [5.1.0]octane-2-acetic acid (Isomer (8b))

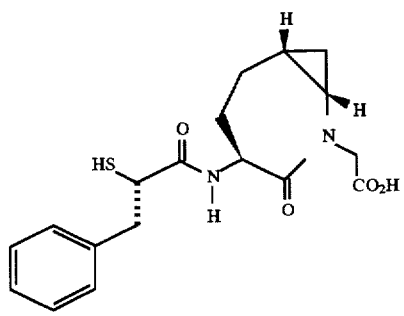

A solution of the title compound of step (D) of Example 7 (307 mg, 0.73 mmole) in Ch₃OH (5.0 ml) was purged with argon for 30 minutes, cooled to 0° C. (ice-salt bath) and treated dropwise with a solution of 1.0 N NaOH (2.96 ml, 4 eq, previously purged with argon for 30 minutes), maintaining the bubbling of argon throughout the addition and length of the reaction. The reaction mixture was stirred at 0° C. for 1.0 hour then brought to pH 2.0 with 5% KHSO₄. The mixture was warmed to room temperature, extracted with EtOAc (2×40 ml) and the combined organic extracts were washed with brine (6.0 ml), dried (anhydrous Na₂SO₄), filtered, evaporated to dryness and dried in vacuo. The crude product was triturated with CH₂Cl₂:hexane (1:8-27 ml) and hexane (25 ml), decanting the supernatant solutions. The precipitates obtained were re-dissolved in a mixture of CH₂Cl₂ and Ch₃OH and evaporated to give Isomer (8a) of the title compound of this Example as a white solid (252.5 mg, 95.4%) with consistent ¹H-NMR, IR, MS and analytical data.

TLC: R_f 0.55 (Silica gel; EtOAc:HOAc- 95:5; UV). m.p.=211–213° C. [α]_D=−16.6° (c0.85, Ch₃OH) MS. (M−H)⁻=361 HPLC: K'=4.89 (UV 220 nm) for peak at 12.56 min (100% S isomer); YMC S-3 ODS-A 6×150 mm; 47% (10% H₂O-90% MeOH- 0.2% H₃PO₄)/53% (90% H₂O- 10% MeOH-0.2% H₃PO₄), isocratic. Anal. for C₁₈H₂₂N₂O₄S: Calc'd : C, 59.65; H, 6.12; N, 7.73; S, 8.85 Found : C, 59.23; H, 6.09; N, 7.67; S, 8.78

Conducting the aforementioned procedure of this Example, using the title compound of step (E) of Example 7 in place of the title compound of step (D) of Example 7, provides the Isomer (8b) title compound of this Example.

EXAMPLE 9

1000 tablets each containing the following ingredients:

| | |
|---|---|
| Compound of Example 1 | 100 mg |
| Cornstarch | 100 mg |
| Gelatin | 20 mg |
| Avicel (microcrystalline cellulose) | 50 mg |
| Magnesium stearate | 5 mg |
| | 275 mg | are prepared from sufficient bulk quantities by mixing the title product of Example 1 and cornstarch with an aqueous solution of the gelatin. The mixture is dried and ground to a fine powder. The Avicel and then the magnesium stearate are admixed with granulation. The mixture is then compressed in a tablet press to form 1000 tablets each containing 100 mg of active ingredient.

In a similar manner, tablets containing 100 mg of any of the products of Examples 2 to 8 can be prepared.

Similar procedures can be employed to form tablets or capsules containing from 10 mg to 500 mg of active ingredient.

What is claimed is:

1. A compound of the following formula I, or a pharmaceutically acceptable salt thereof:

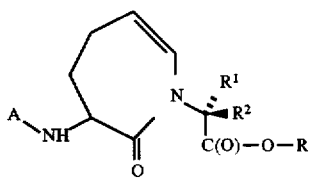
(I)

wherein:

A is

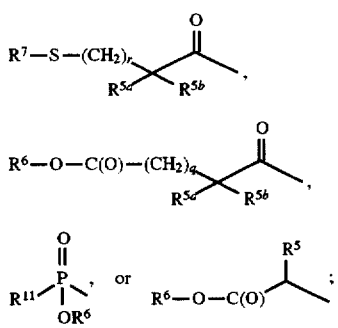

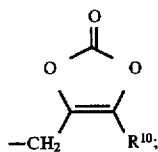

R and $R^6$ are each independently hydrogen, alkyl, substituted alkyl, aryl—$(CH_2)_p$—, substituted aryl—$(CH_2)_p$—, heteroaryl—$(CH_2)_p$—, —$CH(R^8)$—O—C(O)—$R^9$, or

[structure with —CH$_2$ and $R^{10}$]

$R^1$ and $R^2$ are each independently hydrogen, alkyl, substituted alkyl, cycloalkyl—$(CH_2)_p$—, aryl—$(CH_2)_p$—, substituted aryl—$(CH_2)_p$—, heteroaryl—$(CH_2)_p$—, or $R^1$ and $R^2$ may form, together with the carbon to which they are bonded, a 3 to 7 membered carbocyclic ring, where said ring is optionally substituted by alkyl, or by aryl which is fused or bonded by a single bond to said ring;

$R^5$, $R^{5a}$, and $R^{5b}$ are each independently hydrogen, alkyl, alkenyl, cycloalkyl, substituted alkyl, substituted alkenyl, aryl, substituted aryl, heteroaryl, cycloalkyl—alkylene—, aryl—alkylene—, substituted aryl—alkylene—, and heteroaryl—alkylene—, or $R^{5a}$ and $R^{5b}$ may form, together with the carbon to which they are bonded, a 3 to 7 membered carbocyclic ring, where said ring is optionally substituted by alkyl, or by aryl which is fused or bonded by a single bond to said ring;

$R^7$ is hydrogen, $R^8$—C(O)—, or $R^{12}$—S—;

$R^8$ is hydrogen, alkyl, substituted alkyl, cycloalkyl—$(CH_2)_p$—, substituted aryl—$(CH_2)_p$—, or heteroaryl—$(CH_2)_p$—;

$R^9$ is hydrogen, alkyl, alkoxy, or aryl;

$R^{10}$ is alkyl or aryl—$(CH_2)_p$—;

$R^{11}$ is alkyl, substituted alkyl, cycloalkyl—$(CH_2)_p$—, aryl—$(CH_2)_p$—, substituted aryl—$(CH_2)_p$—, or heteroaryl—$(CH_2)_p$—;

$R^{12}$ is hydrogen, alkyl, substituted alkyl, cycloalkyl—$(CH_2)_p$—, aryl—$(CH_2)_p$—, substituted aryl—$(CH_2)_p$—, or heteroaryl—$(CH_2)_p$—, or —S—$R^{12}$ completes a symmetrical disulfide wherein $R^{12}$ is

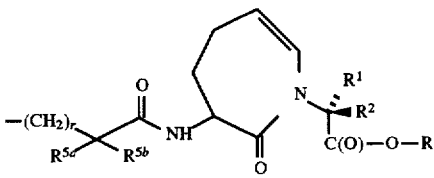

p is zero or an integer from 1 to 6;

q is zero or an integer from 1 to 3; and r is zero or one.

2. A compound of claim 1, wherein

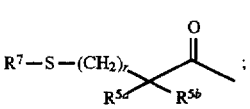

$R^1$ and $R^2$ are each independently hydrogen, alkyl or aryl—$(CH_2)_p$—;

R is hydrogen or lower alkyl;

one of $R^{5a}$ and $R^{5b}$ is hydrogen and the other is alkyl, substituted alkyl or aryl—alkylene;

$R^7$ is hydrogen or $R^8$—C(O)—where $R^8$ is lower alkyl;

p is zero or an integer from 1 to 4; and r is zero or one.

3. A compound of claim 1, wherein said compound is selected from the group consisting of:

[αS-(αR*,2R*,3R*)]-3-[[2-(acetylthio)-1-oxo-3-phenylpropyl]amino]-2,3,4,5-tetrahydro-α-methyl-2-oxo -1H-azepine-1-acetic acid, methyl ester;

[αS-(αR*,2R*,3R*)]-2,3,4,5-tetrahydro-3-[(2-mercapto-1-oxo-3-phenylpropyl)amino]-α-methyl-2-oxo-1H-azepine-1-acetic acid;

[S-(R*,R*)]-3-[[2-(acetylthio)-1-oxo-3-phenylpropyl]amino]-2,3,4,5-tetrahydro-2-oxo-1H-azepine -1-acetic acid, methyl ester;

[S-(R*,R*)]-2,3,4,5-tetrahydro-3-[(2-mercapto-1-oxo-3-phenylpropyl)amino]-2-oxo-1H-azepine-1-acetic acid;

[αS-(αR*,2R*,3R*)]-3-[[2-(acetylthio)-1-oxo-3-phenylpropyl]amino]-2,3,4,5-tetrahydro-α-(1-methylethyl) -2-oxo-1H-azepine-1-acetic acid, methyl ester;

[αS-(αR*,2R*,3R*)]-2,3,4,5-tetrahydro-3-[(2-mercapto-1-oxo-3-phenylpropyl)amino]-α- (1-methylethyl)-2-oxo-1H-azepine-1-acetic acid; and pharmaceutically acceptable salts thereof.

4. A method for the inhibition of angiotensin converting enzyme, comprising the step of administering to a subject in need thereof a compound of claim 1 in an amount effective therefor.

5. A method for the inhibition of angiotensin converting enzyme and neutral endopeptidase, comprising the step of administering to a subject in need thereof a compound of claim 1 wherein A is

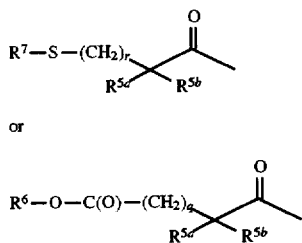

or

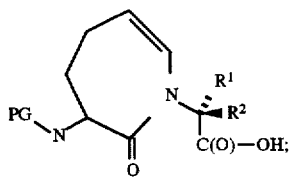

in an amount effective therefor.

6. A pharmaceutical composition comprising a compound of claim 1, and a pharmaceutically acceptable vehicle or diluent.

7. An unsaturated azepinone acid having the following formula, or a salt thereof:

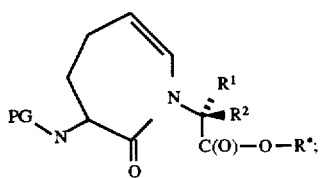

wherein $R^1$ and $R^2$ are each independently hydrogen, alkyl, substituted alkyl, cycloalkyl—$(CH_2)_p$—, aryl—$(CH_2)_p$—, substituted aryl—$(CH_2)_p$—, heteroaryl—$(CH_2)_p$—, or $R^1$ and $R^2$ may form, together with the carbon to which they are bonded, a 3 to 7 membered carbocyclic ring, where said ring is optionally substituted by alkyl, or by aryl which is fused or bonded by a single bond to said ring;

PG-N- denotes a protected nitrogen atom; and p is zero or an integer from 1 to 6.

8. A compound of claim 7, wherein said compound is selected from the group consisting of:

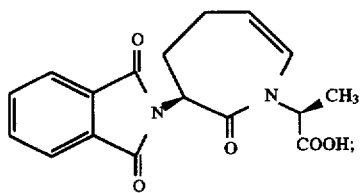

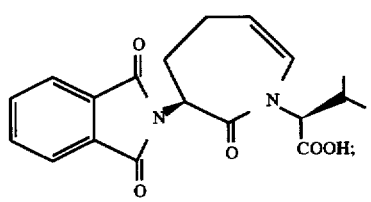

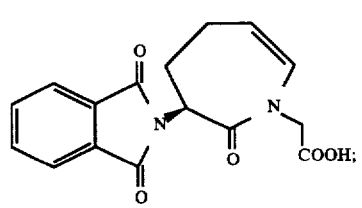

and salts thereof.

9. An azepinone ester having the following formula, or a salt thereof:

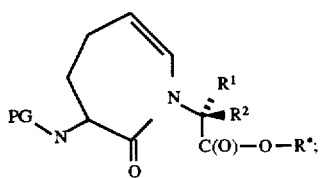

where $R^1$ and $R^2$ are each independently hydrogen, alkyl, substituted alkyl, cycloalkyl—$(CH_2)_p$—, aryl—$(CH_2)_p$—, substituted aryl—$(CH_2)_p$—, heteroaryl—$(CH_2)_p$—, or $R^1$ and $R^2$ may form, together with the carbon to which they are bonded, a 3 to 7 membered carbocyclic ring, where said ring is optionally substituted by alkyl, or by aryl which is fused or bonded by a single bond to said ring; $R^*$ is alkyl, substituted alkyl, aryl—$(CH_2)_p$—, substituted aryl—$(CH_2)_p$—, heteroaryl—$(CH_2)_p$—, —$CH(R^8)$—O—$C(O)$—$R^9$, or

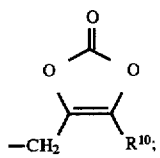

$R^8$ is hydrogen, alkyl, substituted alkyl, cycloalkyl—$(CH_2)_p$—, aryl—$(CH_2)_p$—, substituted aryl—$(CH_2)_p$—, or heteroaryl—$(CH_2)_p$—;

$R^9$ is hydrogen, alkyl, alkoxy, or aryl;

$R^{10}$ is alkyl or aryl—$(CH_2)_p$—;

PG-N- denotes a protected nitrogen atom; and p is zero or an integer from 1 to 6.

10. A compound of claim 9, wherein said compound is selected from the group consisting of:

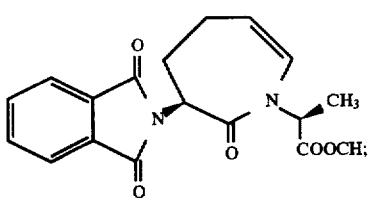

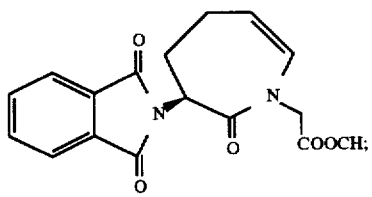

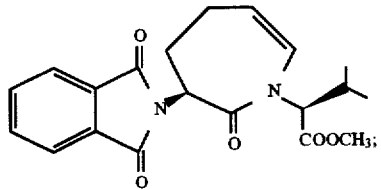

and salts thereof.

11. An amino azepinone ester having the following formula, or a salt thereof:

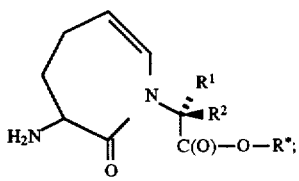

where

R$^1$ and R$^2$ are each independently hydrogen, alkyl, substituted alkyl, cycloalkyl—(CH$_2$)$_p$—, aryl—(CH$_2$)$_p$—, substituted aryl—(CH$_2$)$_p$—, heteroaryl—(CH$_2$)$_p$—, or R$^1$ and R$^2$ may form, together with the carbon to which they are bonded, a 3 to 7 membered carbocyclic ring, where said ring is optionally substituted by alkyl, or by aryl which is fused or bonded by a single bond to said ring; R* is alkyl, substituted alkyl, aryl—(CH$_2$)$_p$—, substituted aryl—(CH$_2$)$_p$—, heteroaryl—(CH$_2$)$_p$—, —CH(R$^8$)—O—C(O)—R$^9$, or

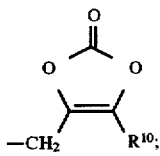

R$^8$ is hydrogen, alkyl, substituted alkyl, cycloalkyl—(CH$_2$)$_p$—, aryl—(CH$_2$)$_p$—, substituted aryl—(CH$_2$)$_p$—, or heteroaryl—(CH$_2$)$_p$—;

R$^9$ is hydrogen, alkyl, alkoxy, or aryl;

R$^{10}$ is alkyl or aryl—(CH$_2$)$_p$—; and p is zero or an integer from 1 to 6.

12. A compound of claim 11, wherein said compound is selected from the group consisting of:

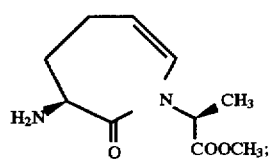

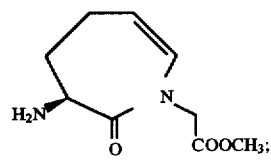

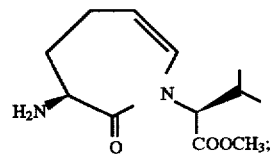

and salts thereof.

13. An azepinone ester having the following formula, or a salt thereof:

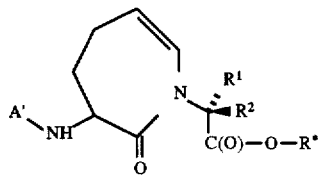

where A' is a group A;

A is

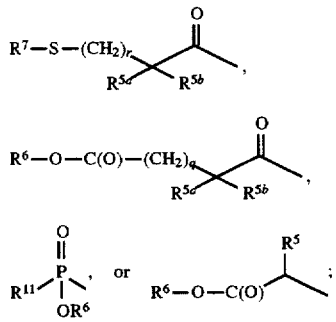

R$^1$ and R$^2$ are each independently hydrogen, alkyl, substituted alkyl, cycloalkyl—(CH$_2$)$_p$—, aryl—(CH$_2$)$_p$—, substituted aryl—(CH$_2$)$_p$—, heteroaryl—(CH$_2$)$_p$—, or R$^1$ and R$^2$ may form, together with the carbon to which they are bonded, a 3 to 7 membered carbocyclic ring, where said ring is optionally substituted by alkyl, or by aryl which is fused or bonded by a single bond to said ring;

R and R$^6$ are each independently hydrogen, alkyl, substituted alkyl, aryl—(CH$_2$)$_p$—, substituted aryl—(CH$_2$)$_p$—, heteroaryl—(CH$_2$)$_p$—, —CH(R$^8$)—O—C(O)—R$^9$, or

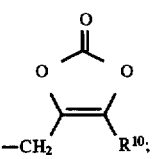

R$^8$ is hydrogen, alkyl, substituted alkyl, cycloalkyl—(CH$_2$)$_p$—, aryl—(CH$_2$)$_p$—, substituted aryl—(CH$_2$)$_p$—, or heteroaryl—(CH$_2$)$_p$—;

R$^9$ is hydrogen, alkyl, alkoxy, or aryl;

R$^{10}$ is alkyl or aryl—(CH$_2$)$_p$—;

R* denotes a group R other than hydrogen;

R$^5$, R$^{5a}$, and R$^{5b}$ are each independently hydrogen, alkyl, alkenyl, cycloalkyl, substituted alkyl, substituted alkenyl, aryl, substituted aryl, heteroaryl, cycloalkyl—alkylene—, aryl—alkylene—, substituted aryl—alkylene—, and heteroaryl—alkylene—, or R$^{5a}$ and R$^{5b}$ may form, together with the carbon to which they are bonded, a 3 to 7 membered carbocyclic ring, where said ring is optionally substituted by alkyl, or by aryl which is fused or bonded by a single bond to said ring;

R$^7$ is hydrogen, R$^8$—C(O)—, or R$^{12}$—S—;

R$^{11}$ is alkyl, substituted alkyl, cycloalkyl—(CH$_2$)$_p$—, aryl—(CH$_2$)$_p$—, substituted aryl—(CH$_2$)$_p$—, or heteroaryl—(CH$_2$)$_p$;

$R^{12}$ is hydrogen, alkyl, substituted alkyl, cycloalkyl—$(CH_2)_p$—, aryl—$(CH_2)_p$—, substituted aryl—$(CH_2)_p$—, or heteroaryl—$(CH_2)_p$—, or —S—$R^{12}$ completes a symmetrical disulfide wherein $R^{12}$ is

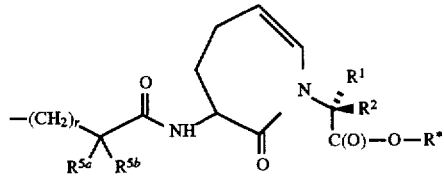

p is zero or an integer from 1 to 6;

q is zero or an integer from 1 to 3; and r is zero or one.

14. A compound of claim 13, wherein A' is

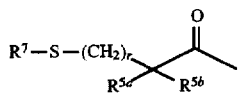

$R^7$ is $R^8$—C(O)—;

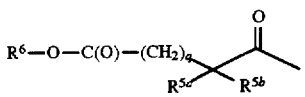

where $R^6$ is other than hydrogen;

where $R^6$ is other than hydrogen; or

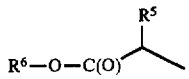

where $R_6$ is other than hydrogen.

* * * * *

UNITED STATES PATENT AND TRADEMARK OFFICE
CERTIFICATE OF CORRECTION

PATENT NO. : 5,750,687
DATED : May 12, 1998
INVENTOR(S) : Jeffrey A. Robl

It is certified that error appears in the above-identified patent and that said Letters Patent is hereby corrected as shown below:

Column 35, line 61, before "substituted aryl-$(CH_2)_p$-" insert
--aryl-$(CH_2)_p$-,--.
Column 36, line 18, "2. A compound of claim 1, wherein" should
read --2. A compound of claim 1, wherein A is--.
Column 38, lines 40 to 54, the structures

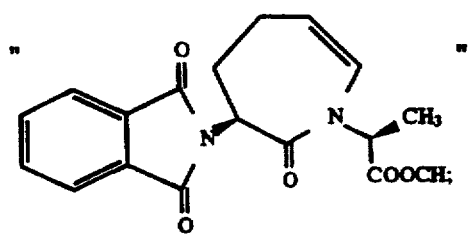 and 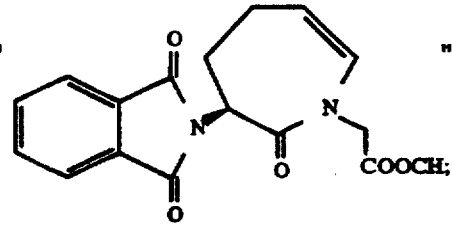

UNITED STATES PATENT AND TRADEMARK OFFICE
CERTIFICATE OF CORRECTION

PATENT NO. : 5,750,687
DATED : May 12, 1998
INVENTOR(S) : Jeffrey A. Robl

It is certified that error appears in the above-identified patent and that said Letters Patent is hereby corrected as shown below:

should read

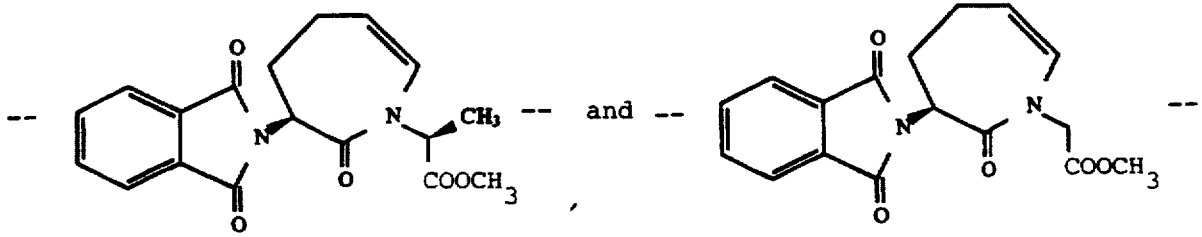

Column 42, line 1, before " $R^7$ is $R^8$-C(O)-; " insert --where--.

Signed and Sealed this

First Day of September, 1998

Attest:

BRUCE LEHMAN

Attesting Officer

Commissioner of Patents and Trademarks